US009770563B1

(12) United States Patent
Freeman et al.

(10) Patent No.: US 9,770,563 B1
(45) Date of Patent: Sep. 26, 2017

(54) APPARATUS FOR TRANSFERRING AND DISPENSING ESSENTIAL OILS AND WAXES

(71) Applicant: Halo Light Works, LLC, Gilroy, CA (US)

(72) Inventors: William Freeman, Gilroy, CA (US); Gil Fernandes, Morgan Hill, CA (US); Jerry Chen, Fremont, CA (US)

(73) Assignee: HALO LIGHT WORKS, LLC, Gilroy, CA (US)

( * ) Notice: Subject to any disclaimer, the term of this patent is extended or adjusted under 35 U.S.C. 154(b) by 0 days.

(21) Appl. No.: 14/542,537

(22) Filed: Nov. 14, 2014

Related U.S. Application Data

(60) Provisional application No. 61/903,964, filed on Nov. 14, 2013, provisional application No. 61/946,904, filed on Mar. 3, 2014.

(51) Int. Cl.

| | |
|---|---|
| ***A61M 11/00*** | (2006.01) |
| ***A61M 11/04*** | (2006.01) |
| ***B67D 7/42*** | (2010.01) |

(52) U.S. Cl.
CPC ............. *A61M 11/04* (2013.01); *B67D 7/421* (2013.01); *A61M 2209/045* (2013.01)

(58) Field of Classification Search
CPC ........................................................ B67D 7/54
USPC ...... 401/1, 2, 9, 11, 95, 128, 198, 265, 267; 222/341, 372, 378, 381, 383.1, 386, 420, 222/421
See application file for complete search history.

(56) References Cited

U.S. PATENT DOCUMENTS

| | | | | |
|---|---|---|---|---|
| 1,390,475 A * | 9/1921 | Toler | A61J 7/0023 30/326 |
| 5,137,183 A * | 8/1992 | Mikulec | A61J 7/0023 222/192 |
| 6,134,790 A * | 10/2000 | Watson | A47G 21/02 30/295 |
| 6,331,085 B1 * | 12/2001 | Schrepf | A45D 34/046 401/122 |
| 2010/0168637 A1 * | 7/2010 | Casey | A45D 34/00 604/3 |

* cited by examiner

*Primary Examiner* — David Walczak
*Assistant Examiner* — Joshua Wiljanen
(74) *Attorney, Agent, or Firm* — Maschoff Brennan

(57) ABSTRACT

An apparatus for manual transfer of a viscous fluid such as essential oil or wax comprises a tip having a depression to accommodate an amount of the viscous fluid and a brim to cause a break in a vapor trail when the amount of viscous fluid is being placed on a heated surface and becomes vaporized; a cap that fits over the tip to prevent unwanted transfer of any remaining viscous fluid to surroundings when the tool resting on a surface; and a handle to allow a user to hold the without contacting the tip.

20 Claims, 24 Drawing Sheets

APPARATUS FOR TRANSFERRING AND DISPENSING ESSENTIAL OILS AND WAXES

CROSS REFERENCE TO RELATED APPLICATIONS

The present application claims priority to U.S. Provisional Patent Application No. 61/903,964, filed Nov. 14, 2013, entitled "Essential Oil Applicator Tool," and U.S. Provisional Patent Application No. 61/946,904, filed Mar. 3, 2014, entitled "Tools for Dispensing Essential Oils and Waxes," each of which is incorporated herein by reference in its entirety.

BACKGROUND

Field

The present application is related generally to tools or devices for transferring small amount of viscous fluids, and more particularly to apparatus for transferring and dispensing essential oils and waxes.

Description of Related Art

Essential oils and waxes are used in many applications from medicinal applications like aroma therapy to air fresheners. Waxes are merely high molecular weight oils that solidify at room temperature. Many devices (or applicators or tools) on the market are designed to transfer these oils and waxes (referred to hereafter as "material" or "materials") from their containers to a heated surface of a vaporizing device for vaporization. Most of the currently available tools are minor variations from laboratory spatulas and dental tools, for example, dental picks. There are a number of problems with the current tools, including:

1) Too little material being transferred per application so that multiple applications have to be used to transfer a certain amount of material;
2) Too much redeposition of material, meaning that, as the material is vaporized from the tip of the tool or from the heated surface, the vapor tends to condense or redeposit material on the cooler parts of the tool, which not only makes a bit of mess but also may waste material;
3) Lack of isolation from the surroundings, so that the tool makes a mess and wastes material by inadvertently depositing it on whatever surface the tool is placed on (for example, when the tool is placed on a table, unused material or redeposited material on the tip and/or sides of the tool can easily touch the table surface, thereby transferring material to the table surface, resulting in wasted material);
4) Difficult to efficiently move material from the applicator tool to the vaporizing device, which results in a waste of time and material, as well as potentially damaging the vaporizing device (for example, dental pick like tools can easily damage the expensive heating coils that heat and vaporize the transferred material), and
5) Limited ability to store material in the tool for multiple applications or to meter out the material in a known fashion.

SUMMARY

An apparatus (or tool) for manual transfer of a viscous fluid such as an essential oil or wax has been designed to solve various problems associated with the conventional tools used for similar purposes. As one example of a common use, the apparatus can be used to transfer a solution or paste to an element that vaporizes it for aroma therapy applications. In certain embodiment, the apparatus is capable of: (1) transferring the right amount of material in each application so that multiple transfers are kept to a minimum; (2) transferring the material in a way that does not cause unnecessary waste of the material due to the material sticking to the tool; and (3) minimizing redeposition of the vapor from the material on the apparatus when the material is being transferred to a hot surface.

In certain embodiments, an apparatus designed for manual transfer of a viscous fluid comprises a tip having a depression to accommodate an amount of the viscous fluid, a brim to cause a break in a vapor trail when the amount of viscous fluid is being placed on a heated surface and becomes vaporized, a cap that fits over the tip to prevent unwanted transfer of any remaining viscous fluid to surroundings when the apparatus is resting on a surface, and a handle to allow a user to hold the apparatus without contacting the tip.

According to certain embodiments, the cap is a screw on cap, and/or the handle is hollow to accommodate one or more useful tools or hold additional amount of material for later transfer.

In certain embodiments, the tip is detachable, and the tip and the handle can be made of different materials. In certain embodiments, the handle includes a threaded tip to allow the user to easily replace the tip. In certain embodiments, the handle has a heat dissipating structure.

In certain embodiments, the apparatus further comprises an umbrella washer or nut separate from the tip such that both may thread onto the apparatus. The umbrella washer acts as a lock nut to hold the tip at a user selected point on the end of the tool handle, allowing adjustable thermal management of the tip In certain embodiments, the tip can be a dynamic tip, in the sense that it has moving parts, or mechanism that aids in the material transfer process, such as a tip with a plunger that is actuated by pressing or twisting an actuating mechanism.

In certain embodiments, the tip or head is removable, as is the umbrella nut that may be optionally used in the case of loading material to a hot surface.

In certain embodiments, the apparatus further comprises means of storing sufficient material so that the apparatus may be used multiple times before requiring refilling. In certain embodiments, the apparatus further comprises a mechanism for precisely metering the material to a loading bay or directly out of the tool. In certain embodiments, the apparatus comprises means for monitoring the amount metered out and/or the amount remaining in the tool. In certain embodiments, the apparatus can be loaded using a cartridge system that allows a precisely known quantity of material to be loaded with minimal effort and mess. In certain embodiments, the cartridges are designed to allow a device that normally meters out viscous fluids to meter out much less viscous fluids because the cartridge acts like a self sealing one way valve.

In certain embodiments, the cartridges are labeled/printed/chipped in a way that allows tracking of the cartridge by microwave or optical or radio frequency scanning or by other means. In certain embodiments, the cartridges are coated or impregnated with a material that allows identification of the cartridge and/or the material in the cartridge and/or some property or aspect of the material in the cartridge.

In certain embodiments, a threaded twist mechanism is used to multiply the users force for driving the dispensing mechanism. In certain embodiments, a twist mechanism allows the user to dispense variable quantities of material based on the degree of rotation of the twist mechanism actuator. In certain embodiments, a twist mechanism is used for loading the material into a dispensing chamber where the material can later be ejected by a push mechanism.

DESCRIPTION OF THE EMBODIMENTS

Figure 1:
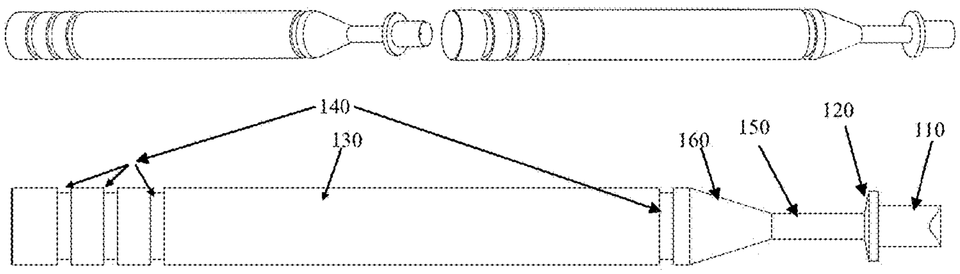
FIG. 1 is a diagram illustrating a one piece tool with a tip depression visible along with a wireframe sketch with various features labeled according to certain embodiments.

In the following the material being transferred is referred to as simply "material" or "transfer material."

There is a logical progression of sophistication in the design of transfer tools. The simple dab-and-place tool with no moving parts may be improved to contain and deliver a single dose and designed to minimize the probability of damaging the vaporizing device. An obvious improvement on single dose delivery, is a tool that can store enough material for multiple doses and consistently meter out that material. A further enhancement would be to provide the user with some indication of how much material remains to be dispensed. And finally one may wish to allow the user to adjust the quantity dispensed. What follows are the design considerations, materials and surface treatment considerations, and manufacturability considerations necessary to arrive at commercially viable essential oil transfer and dispensing tools for hand held personal use. One might consider transfer tools as the simplest or most primitive embodiment of the dispensing tool spectrum.

The example embodiments are described roughly in the order of the list of enhancements described in the previous paragraph, which also tends to address the disadvantages of existing tools roughly in the order they were listed in the background section.

More material may be transferred by increasing the area of the transfer tool tip. For example, a pick may be expanded into a cylinder. For a given overall size the area may be further increased by creating more complex shapes, e.g., a cylinder with a concave depression at the end. The tool may have multiple and interchangeable tips, where the tip geometry is tailored to best suit transferring material within a given range of rheological properties, with viscosity usually being the most important rheological property.

When vaporized most materials will tend to climb up the sides of whatever was used to transfer the material, due to aerodynamic skin effect called the Coanda effect. Assuming that the transfer tool is used to transfer to an already hot surface, as the hot vapors climb up the sides of the transfer tool some portion of the vaporized material will condense on the cooler portions of the tool and may leave deposits of material in undesirable places. The embodiment described here to remedy this problem is an expanded portion of tool designed to form a break in the rising vapor stream. In the case of round tool this makes the tool tip look like an inverted hat, where the vapor break is the brim of the hat.

To keep the tip of the tool away from surfaces when the tool is not in use, the comfort grip is designed to be a greater diameter than the widest part of tip. An added innovation can be had by making the handle of the tool tapered in a way that not only tilts the tip up off the surface the tool is resting on, but also causes the tool to roll in circles instead of the rolling in a straight line and falling off the edge of the surface it is resting on. Of course, the rolling problem may be solved by making the tool handle in a shape other than round, e.g., hexagonal or elliptical. All of the embodiments here are round because round results in a lower manufacturing cost.

The difficulty in moving material from the transfer tool to the vaporizing device may be remedied by tip geometry and/or appropriate surface treatments. In cases where the modifications to static tool do not yield a satisfactory result, a more sophisticated design, where the tool has a movable piston for ejecting the material into or onto the vaporizing surface, may be used. Of course this more sophisticated design will still benefit from appropriate tip geometry and surface treatments.

In certain embodiments, the hat or umbrella like tip is design so as to cause a break in the vapor trail to prevent redeposition on the rest of the tool. Building on this insight are the following levels of sophistication in tool design:

1) A static tool that may include multiple interchangeable tips.
2) A tool with an ejection mechanism that deliverers a single dose and must be reloaded each time.
3) A tool that can deliver multiple doses, where an indicator mechanism allows the user to know the amount material left in the tool and the amount of material ejected may be set by the user by an adjustment mechanism.

Note that the tool tips may be made in various sizes to accommodate the different sizes of vaporizing devices. The tools with interchangeable tips may also have tip versions that are designed to enhance the vaporization process and/or the user's experience, e.g., a vapor concentrator cap with a small hole so that user may control the vapor concentration by partially covering the hole with a finger.

Also note that there are two dichotomous ways in which this tool may be used. Material may be transferred to a hot surface for immediate vaporization, in which case the vapor break feature is a useful part of the design. In addition to transferring to a hot surface, the tool may also be used to transfer material to a cold surface for later vaporization, in which case the ease of release of the material from the tool becomes a useful feature. In the case of transfer to a hot surface, the heat would generally lower the viscosity of the material to the point where release is no longer an issue. Frequently the same tool can be used in both modes, which is some of of the embodiments that follow include the hat feature to ameliorate redeposition, as well as appropriate surface treatments to facilitate as clean a release as possible while still retaining the material until the user wants it released.

Note that the static tool is primarily designed to be used to transfer material directly onto the hot vaporizing surface. Thus, the vapor break could be more important than material release features, since the material will generally become much less viscous upon heating making release a non issue.

Following are a list of features of the tool according to certain embodiments:

1) There are one or more rings 140 on each end of the barrel 130. (Illustrated in FIG. 1.) They may be used to retain rubber or other polymer bands or o-rings to make the grip more comfortable and tool use easier. The reason for there being band(s) 140 at each end of the barrel is so that when placed on a surface neither the tip 110 nor the umbrella 120 will touch the surface. This keeps any material on the tip area from messing up the table surface, which may result in material being wasted. Also, notice that the umbrella is slightly smaller than the barrel, so even without bands the tip will not touch any surface when the tool is resting on a flat surface such as a table or bench top. However, sufficient material buildup on the umbrella circumference may result in material being transferred to unintended surfaces if the o-rings or polymer bands are not present.
2) The particular embodiment illustrated in FIG. 1 shows rings on both ends of the tool. If the rings at the left end of the tool are the same size as the ring at the right end of the tool then there is the possibility for the tool to role a long distance on an inclined surface. For example, it can easily role off a table top. However, if the ring near the tip is larger or the rings distal to the tip (left end in FIG. 1*c*) are not present, then the tool will not sit parallel to the table, but rather sit at an angle where the tip is higher than in the case where the rings are the same size and the tool rests parallel to the table surface. This inclined tool position has at least two advantages:
   1) The tip is further from the surface upon which the tool rests, further reducing the chance that material will inadvertently transfer from the tool to unintended surfaces.
   2) The fact that tool is inclined to the surface upon which it rests implies that should the tool role it will role in circles (as opposed to role in a straight line as in the case of uniform size rings on both ends of the tool), which will dramatically lessen the chance it will roll off the edge of the supporting surface. Thus, it is less likely that the tool will roll off the table if the rings on one end are a different size than the rings on the other end. Note that if rings are to made different sizes, it makes the most sense to have the ring(s) proximal to the tip be larger than rings more distal to the tip so as to minimize the probability of the tip touching unwanted surfaces and transferring material to places where it is not wanted.

Clearly the angle created by using different size rings may not be great and while making the ring near the tip larger than the rings more distal from the tip, may cause the tip to tilt upwards slightly and thus be further from the surface the tool is resting on, the same break in linear rolling can be achieved by decreasing the size of the ring near the tip. This can cause the tip to be somewhat closer to the surface the tool is resting on and thus increase the likelihood that of material that may have collected around the edge of the hat touching the surface the tool is resting on.

The goal of stopping the tool from rolling off surfaces by changing the tendency to roll linearly to a tendency to roll in a circle can be achieved in number of ways. For example, taper the handle (called the barrel in the figures below) of the tool or vary the diameter of the polymer rings that are attached to the tool handle. It makes the most sense to vary the diameters in ways the increase, rather than decrease the distance of the tool tip to the surface it rests on; however, this is not an absolute requirement. If one is willing to move away from the tacit assumption that the bands have to be uniform cross section like o-rings or rubber bands, then bands may be used that are polygonal outside and circular inside as a simple solution to the problem that involves no modification to the cylindrical shape of the tool. Of course, there is nothing expressed or implied here to prevent the combination of two or more of these techniques.

Figure 5:
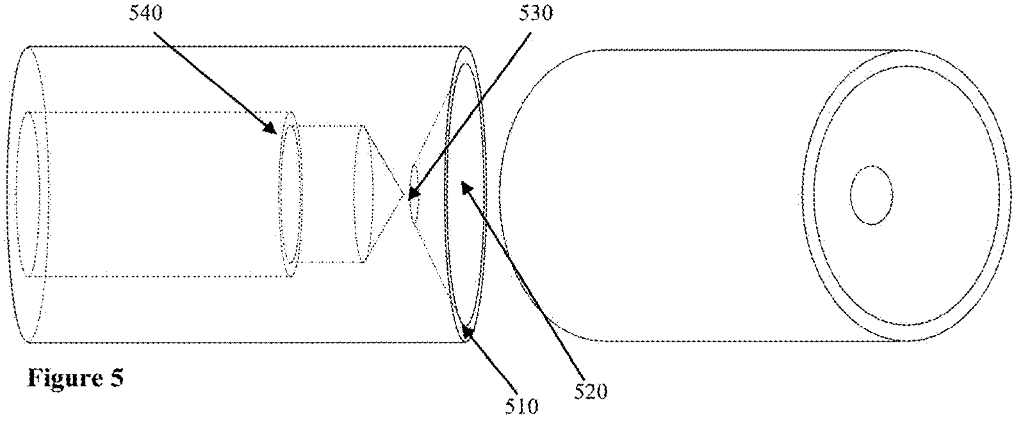
FIG. 5 is a diagram illustrating a variation of tip geometry that may be appropriate for softer materials according to certain embodiments.
Figure 6:
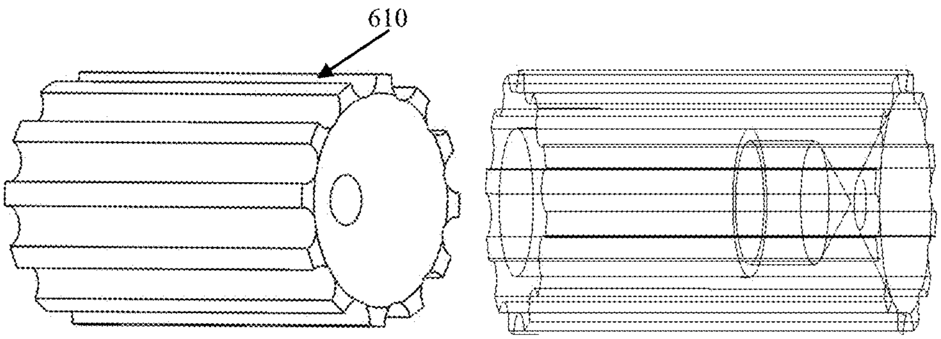
FIG. 6 is a diagram illustrating another embodiment of the tip geometry, where the outside of the tip is fluted so that it can be used more like a honey dipper.
Figure 7:
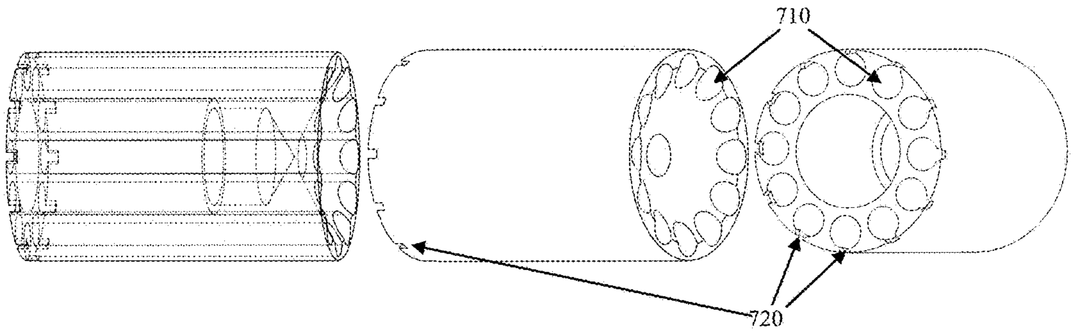
FIG. 7 is a diagram illustrating yet a further embodiment of the tip geometry, where there are a ring of holes for holding more fluid materials.

The size and shape of the tip determines how much material is transferred per application. The diameter of the tip and whether it is flat, convex, or concave determines to first order how much material is transferred. FIGS. 3, 5, 6, and 7 show enlarged views of tips whose end faces are all concave. The type of material the tool is made from, surface features, and surface treatments determine the adhesion properties of the transfer material to the tip. Of course, other parameters such as tool temperature and the like will also affect the adhesion properties. Note that there is no implied exclusion of the possibility of a combination of tip features. For example:

1) The tip may contain a hole in the center for packing the transfer material so that when transferred to a hot surface it melts out as the tip heats up.
2) Making the exterior of the tip fluted, as in FIG. 6, allows one to use it like a honey dipper due to the increased area. Clearly the flutes 610 could be grooves of any shape or orientation. An example may be making them twisted like the threads on a bolt, where the thread shape, depth, and pitch may be tailored to the rheological behavior of the transfer material and thermally dependent changes in that rheological behavior.
3) The tip may be made from a porous material, which may more effectively transfer very low viscosity materials.
4) The tip (and possibly some portion of the tool beyond the tip, such as a capillary 710 that extends up into or through the shank) might contain one or more cavities 720 designed to hold material by capillary action, as the example in FIG. 7 illustrates.
5) FIG. 5 illustrates a tip with a broad lip 510 and a hollowed interior 540. Heat is transferred to the tool largely through the part that is in intimate contact with the heated surface that vaporizes the material. The larger the contact area the faster the tip will heat. Thus, the first order tuning of rate of heating of the tip is determined by how much of the tip is in contact with the heated surface the material is being transferred to. The width of the lip is an example of one way the rate of heat transfer to the tool can be controlled.
6) A wicking structure may be surrounded by a non-porous structure that causes the wicking structure to act like a reservoir for holding the transfer material.
7) The above mentioned wicking structure might be loaded by reducing the viscosity of the material, say by heating. The material is firmly retained until the tip (and hence the contained or attached wicking structure) is heated and the material can flow to the tip and onto the intended surface for vaporization. A tacit assumption here, for this to work well, is that surface of the wick and tip is such that the heated portion has a higher affinity for the material than cooler portions so that material tends to flow to the warmer areas.

The flat bottom 530 is a feature that occurs in the tip designs according to certain embodiments. The bottom may be flat or rounded or some other shape. The point is that cleaning the conical tip cavity 520 will be easier if the bottom is not the apex of the cone. The flat bottom feature reduces manufacturing costs for some common processes such as CNC machining Note that there is nothing implied here that the tip must be made from a single material. These examples imply that there is merit to a tool with interchangeable tips or at least a range of tools should be offered with different tip designs for different transfer material properties.

Figure 3:
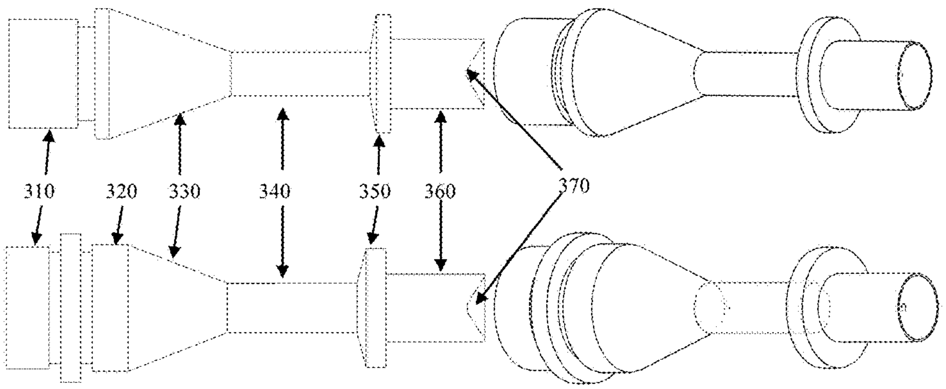
FIG. 3 is a diagram illustrating two versions of a removable head designed to be used with a tool body of FIG. 4 according to certain embodiments.
Figure 4:
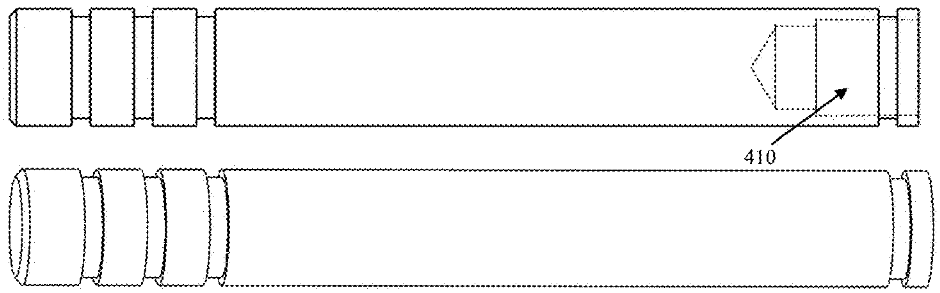
FIG. 4 is a diagram illustrating a tool body designed for one of the removable heads of FIG. 3 according to certain embodiments.

An embodiment of a tool designed to have removable or interchangeable heads, threaded tail 310 plus taper 330 plus shank 340 plus umbrella 350 plus tip 360 with the depression 370, is shown in FIG. 3 and the associated barrel 410 is shown in FIG. 4.

A non-essential, yet useful feature in an essential oil transfer tool is the ability to cover or otherwise isolate the portion of the tool that comes in contact with the material to be transferred from the surroundings. Feature 320 of FIG. 3 is an external thread designed to accept a screw on cap that is intended to keep residual material from being transferred unintentionally when the tool is not in use. By not threading surface 310, a tool designed to accommodate a slip-on cap may be made. Some example isolation techniques would be a simple cap that fits or threads onto that portion or the ability to retract said portion in a way that effectively isolates it from the surroundings. Of course, while in use the most obvious way to isolate said portion from the surroundings is to make the diameter of that portion smaller than the diameter of the tool (minor diameter if the tool is some shape other than circular) and make the mass balance such that the tool rests on horizontal surfaces with the material coated portion suspended off the surface so that there is no contact with surface the tool is resting upon. Concealment via cap or refraction, as a means of isolating the tip or active part of the tool from the surroundings when not in use, are only two of many possibilities. For example, a little bigger handle would enable one to pivot the tip into a pocket in the handle that would effectively isolate the tip from the surroundings while not in use. Along the same line of thinking, the threads 320 that may be use to attach a cap, may also be used to turn the head around when not in use and refasten it so that the tip with residual material would then be encased by the barrel.

Figure 10:
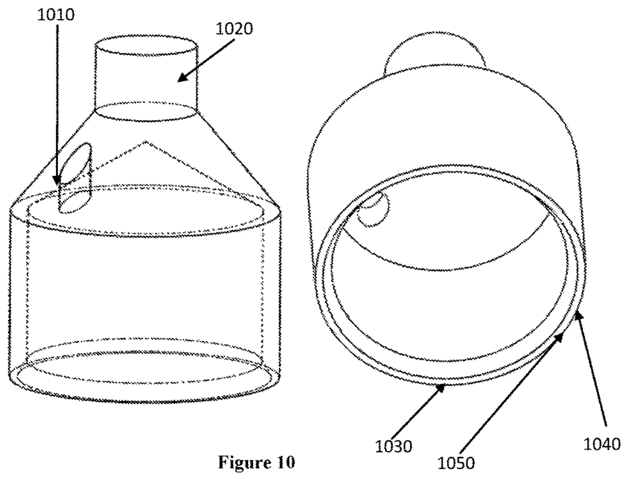
FIG. 10 a diagram illustrating a stylized vapor concentrator that can thread into the same tool body as the heads shown in FIG. 3, according to certain embodiments.
Figure 11:
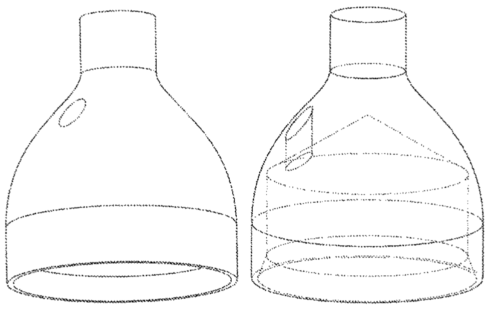
FIG. 11 is a diagram illustrating a sleeker more commercially viable version of the vapor concentrator according to certain embodiments.
Figure 12:
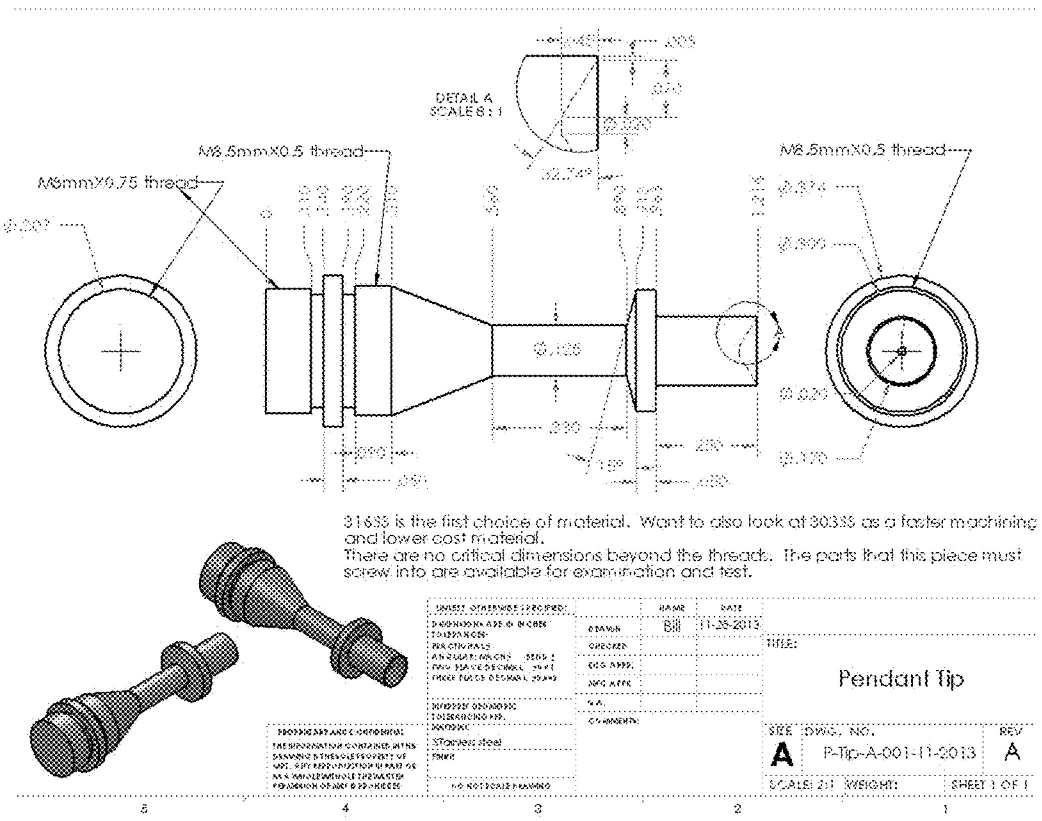
FIG. 12 is a mechanical drawing of the removable tip shown in FIG. 3 designed to accept a threaded cap, according to certain embodiments.
Figure 13:
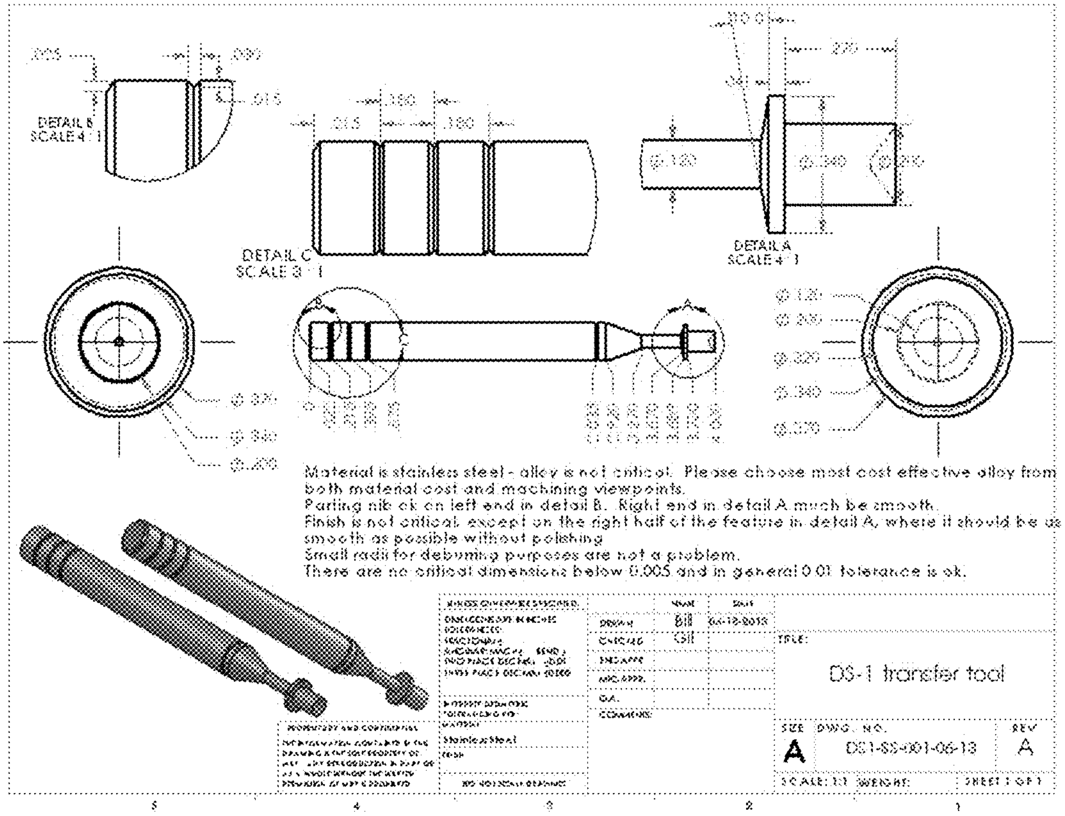
FIG. 13 is a mechanical drawing of a one piece applicator according to certain embodiments.
Figure 14:
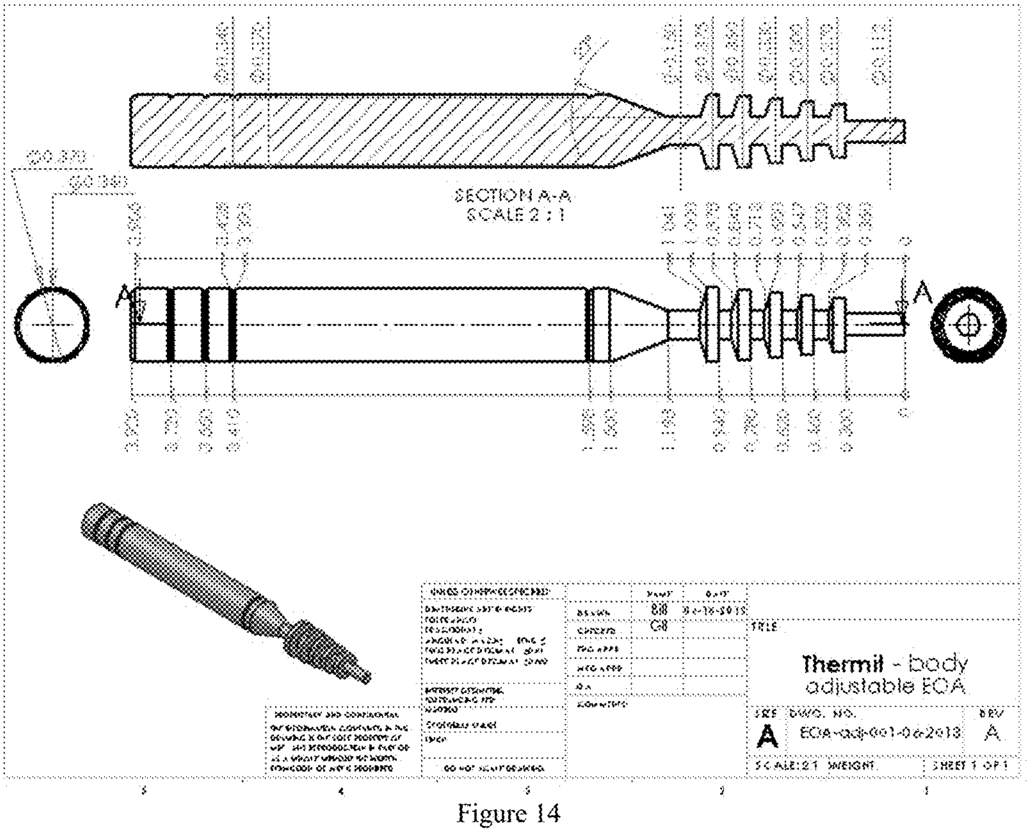
FIG. 14 is a mechanical drawing of the Thermit tool designed for heavier use and has more sophisticated thermal management capabilities according to certain embodiments.

FIGS. 10 and 11 show a vapor concentrator head that may be attached to the barrel of FIG. 4 by the threaded end 1020 and is designed to cover the active portion of a vaporizer while in operation to capture the vapor so that the user can inhale a more concentrated vapor. The hole 1010 is designed to partially covered to control the amount of air mixing with the vapor and thus control the concentration of the vapor air mixture at the point of inhalation. The edge break 1030 eliminates what could be a sharp edge 1050. The tapered lip 1040 makes for a better seal and relaxes tolerances. FIG. 11 illustrates a more sleek looking version that is closer to what could be a commercially viable version.

Since the tool may be used to transfer material to a hot surface, the shaft or relieved shank has a tapered portion 160 and a straight portion 150 behind the umbrella that is reduced in diameter to limit heat flow. This particular embodiment is made from a single material, but there is nothing to prevent one from making this tool from more than one type of material, where the most appropriate material is used in each portion. A follow-on example to the 5th example of feature 3 above, where the rate of heat flowing into the tip is controlled by the area of contact with the hot vaporizing surface, is to limit the rate of heat flow out from the tip through the shank. Since most of the heat flow away from the tip, that there is control over, will be through the shank, the shape, choice of material, and length may all be used to tailor the rate of heat flow from the tip.

There is an advantage to the tool having low thermal conductivity, so this particular embodiment of made from stainless steel. In a multiple material embodiment the tool tip should have a thermal conductance higher relative to the portion after the tip. An exception to this is discussed below in a second example.

The umbrella portion is designed to solve the problem of vaporized material redepositing on the cooler sections of the tool. In applications where material is transferred to a hot surface, the vapor tends to hug the tool. This is a low velocity Coanda effect. The umbrella effectively breaks the rising vapor stream so that there is no (or very minimal) redeposition beyond the umbrella. Material that redeposits on the sides of the tip will generally melt off as the tip warms. The reduction in thermal conductance of the tool after the umbrella aids in this re-melting of the transfer material. In the case of the tool being made from a single piece of material it is only the reduction in shaft diameter that decreases the thermal conductance. Clearly in the case of a multipart tool, changing the relieved shaft or the barrel to a lower thermal conductivity material will also work well to reduce the heat flow to the portion the user holds and to reduce the cooling rate of the tip. Of course, using one material makes the tool easier to manufacture. The tradeoff here will be that the better isolated the tip is so that it heats quickly and releases all the material to the vaporizer surface, the slower the tip will cool, implying the longer the user has to wait between uses.

Figure 2:
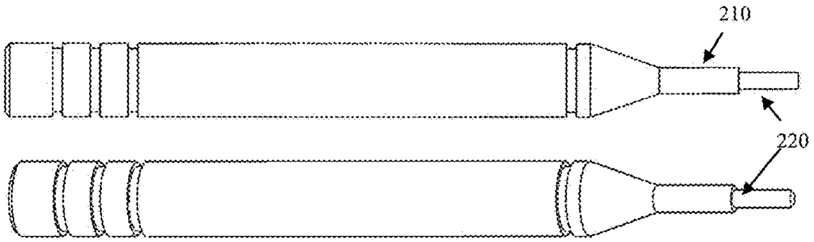
FIG. 2 is a diagram illustrating a barrel design with separate umbrella and tip according to certain embodiments.

The barrels shown in each of the embodiments so far, are shown as solid pieces of metal. There is nothing expressed or implied here that would prevent the barrel from being hollow, or having a cap on the end distal from the tip. This opens up the possibility of tools with cavities for storing extra transfer material, storing different style tips, or other useful tools. An example in the last category is a small scoop or spade attached to a cap that attaches to the distal end of a hollow barrel that could facilitate the user manipulating the transfer material before loading the tip. An example in the second category is to hollow out the back end of the barrel 210 shown in FIG. 2, where the threaded end 220 is designed for the user to change the tip at will. The cavity in the end can then contain several tips and umbrella nuts or several hats, where a hat is a tip and umbrella combined into a single piece.

Figure 8:
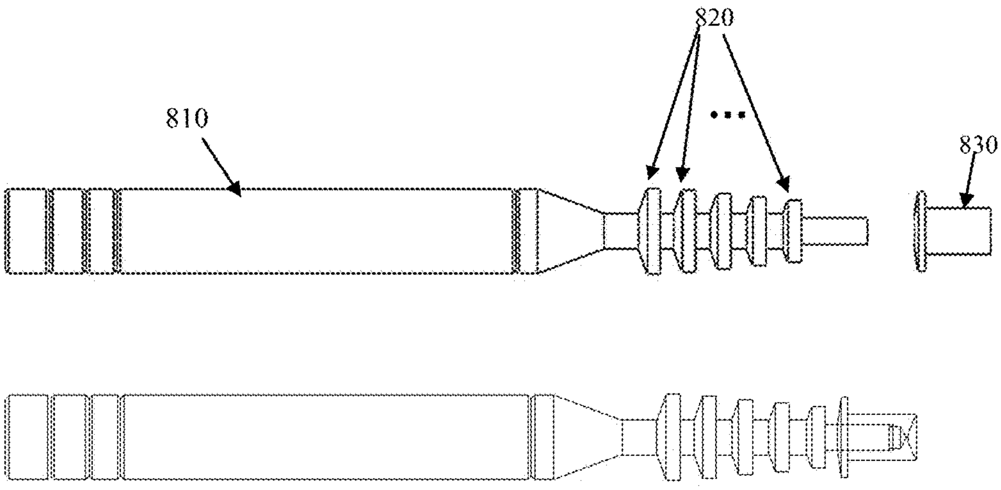
FIG. 8 is a diagram illustrating an exploded view of a "thermit" tool with a one piece head, along with the collapsed or assembled view, according to certain embodiments.

In the event that the tool is used in rapid succession on hot surfaces, a way to dissipate the excess heat must be incorporated in the design. One embodiment of this principle is shown in FIGS. 7 and 8. A description of design features associated with this embodiment follows.

Note that stainless steel, SS, is a relatively poor conductor and transmits heat more slowly than aluminum (a relatively good thermal conductor), and that the ratio of thermal conductivities is at least 20:1 in favor of the aluminum. Thus, if the tip is too thin, the heated surface that vaporizes the oil will be cooled quickly and the barrel of the applicator may become hot in the process. If the tip thickness and/or length is too great, then the SS will retain too much heat and the waiting time for it to cool off between uses will be annoyingly long. Thus, there may be an optimal thickness for each person's use pattern and each combination of materials for making the transfer tool. How long the tip stays hot after each use is determined by the mass of the tip, the heat capacity of the tip material, the thickness of the tip (which determines how far the heat has to flow to get to the high conductivity aluminum), and the thermal conductivities of the tip and barrel. The behavior of the material on the tip is primarily determined by mechanical surface features, surface activity, thermal conductivity, and heat capacity of the tip material and the rate of heat transfer and dissipation from the portion of the tool the tip is attached to.

Figure 9:
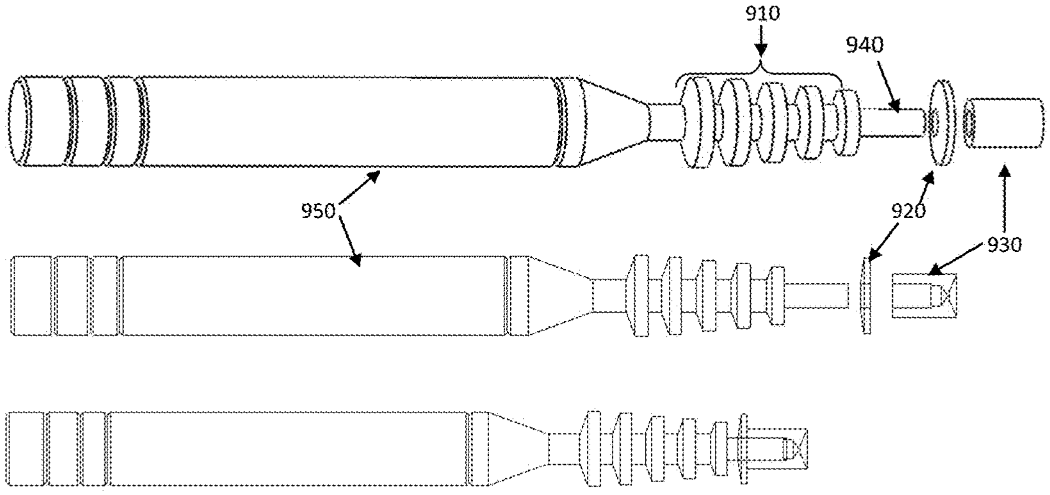
FIG. 9 a diagram illustrating, both assembled and apart, a thermit tool where the head end is made from two separate pieces that thread onto the body according to certain embodiments.

FIG. 8 shows a fixed hat 830 version of the Thermit tool and FIG. 9 shows an adjustable hat version of the tool. The SS tip (which could also be made from titanium or other refractory and biologically friendly materials) threads onto (press fits or otherwise attaches to) the aluminum barrel. The umbrella 920, which is now a separate piece and also threaded, is used to lock the tip 930 in place. A knurled umbrella section would make the tool adjustable without any kind of wrench. This tool may be tailored to the use pattern of the owner. In certain embodiments, the rate of dissipation of heat is determined in part (at least the part that is user adjustable) by how much the pagoda stem 940 threads into the tip. The umbrella may be made of the same material as the tip or a different material depending upon the application.

Following is a list of a few features and/or design criteria for the tool according to certain embodiments.

- The pagoda structure 820 & 910 is designed to dissipate the heat from the tip before it gets to the handle 810 & 950.
- The reason for the inverted pagoda is to make sure that the break in the rising vapor stream created at the tip and broken by the umbrella (breaks the Coanda effect vapor stream) stays broken.
- Aluminum is both lighter and more thermally conductive than brass (but less conductive than copper). Ideally the neck joining the pagoda section to the handle section should be as narrow as possible without compromising structural robustness. The reason for not using copper (other than weight) is that too high a thermal conductance will conduct the heat past the pagoda section before it has time to dissipate. It may turn out that aluminum is also too conductive, but calculations suggest that aluminum is at the upper end of the useful thermal conductivity range.
- The solid handle has sufficient mass so that what heat does make it through the pagoda section will not heat the handle very rapidly. Of course, making the barrel out of two different materials, where the portion the user holds is made of a low thermal conductivity material and the pagoda structure is some higher thermal conductivity material, solves the problem in a way that eases restrictions on the mechanical design. This way the mechanical design can focus more on weight and balance, as well as appearance.

To recap the above, FIG. 8 shows a tool with a fixed interface between the hat and barrel. A more versatile embodiment is illustrated in FIG. 9, where the head is composed of separate umbrella and tip pieces. The umbrella forms a lock nut for the tip so that the interface area between the head and barrel may be adjusted by how far the tip is threaded onto the barrel. This lets the user set the thermal performance in addition to making the tip interchangeable.

In certain embodiments, the performance of the static tool is grossly determined by the tip material, which determines the thermal conductivity and the surface tension between the tip and transfer material. The tip shape and wall thickness further modify the apparent surface tension, amount of material transferred and the thermal conductance. A secondary modification of thermal conductance is user settable by adjusting the thread contact area between the tip and the barrel.

There is nothing implied here limiting the use of the tool to simple pin transfer. Also, the materials used in the example embodiments are in no way intended to limit the range of materials for various parts of the tool. For example, one might heat the tool with either an internal or external heater to load a porous reservoir and meter out the material by thermal conduction from touching the tip to a hot surface or possibly heating a portion of the tool at a desired rate to a desired temperature to establish the desired metering of transfer material. In general, one might electrically, optically, or thermally change the surface tension of the tip or any part thereof, viscosity or surface tension of the transfer material, or both.

Although current usage of this kind of the essential oil applicator is generally for transfer of material to a heated surface that results in vaporization of the transfer material and so the above examples were oriented toward heated surface vaporization, there is nothing implied in the above description that restricts this tool to a particular mode of vaporization. For example, piezoelectric vaporization at temperatures less than the vaporization temperature may also be used with this tool. The minor modifications for use with piezoelectric vaporizers is well within the scope of the above describe gamut of possible modifications. A further example is transferring material to a carrier solution which is then vaporized by various means. Such a carrier solution might form an azeotrope for uniform vaporization of the mixture. A low viscosity carrier solution might be used with a spinning disc or compressed air atomizer to achieve vaporization at a lower temperature.

So far the problem of loading a hand held vaporizer without damaging the coil has not been addressed. Note that if the material being transferred is not viscous then there are numerous existing ways to transfer the material, e.g., a syringe.

Figure 15:
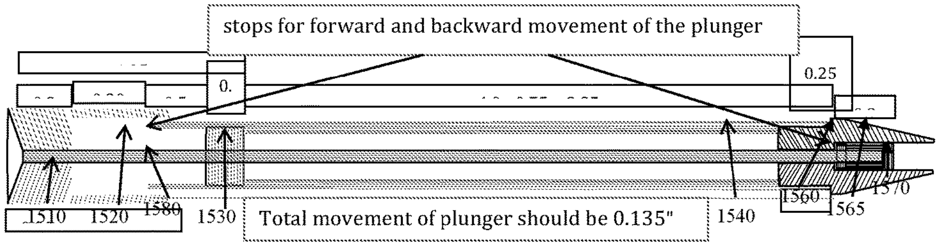
FIG. 15 is a diagram of a basic dynamic essential oil dispenser or loader tool according to certain embodiments.

FIG. 15 illustrates one possible embodiment of the dispenser concept. The hollow part of the tip 1570 may be loaded by pressing the material into the tip. The tip is then put near the device to be filled and the cap 1510 is depressed (syringe style) forcing a slug of material out of the tip onto the vaporizing surface or into the vaporizer chamber. The numbers in rectangles are the measurements in inches of the subtended feature. Note that the scale of the sketch is not uniform. The scale changes somewhat to make the illustration easier to understand.

The basic action is like that of a ball pen. The left end of the rod 1540 in FIG. 15, whose diameter is reduced sufficiently to slide through and be guided by the bushing 1530, either threads into or presses into the cap 1510. When the cap is depressed to eject a slug of material, the maximum travel is determined by the distance from the inside of the cap where the rod 1540 inserts, to the edge of the barrel 1580, which is also shown by the left most arrow from the stop-position note of FIG. 15 and is 0.20" in this design. The tacit assumption here is that the completely compressed spring 1520 length is less than the distance from the left most edge of the bushing to the left barrel lip, 0.50" here, that the cap closes out on when fully depressed. Note that the left most edge of the plunger 1560 closing out on the surface formed by the bore diameter reduction in the tip limits the extent to which the spring can push the cap axially away from the barrel, thereby causing the plunger to retract.

The Embodiment Shown Here has Several Notable Features

The plunger 1565 is a close fit to the wall of the tip bore only at the head and tail ends of the plunger. The relief along most of the plunger prevents material that sticks to the wall of the tip bore from creating too much friction with the plunger and causing it to stick. Another way to view the function of the plunger relief is that it reduces the surface area available to stick to residual material left on the bore wall of the tip.

The cap is always under spring tension. What keeps the cap from coming off is a stop that is either the face of the bushing distal to the cap, or the plunger stopping on the necked down bore of the tip. In the case of the bushing acting as the stop, there must be something larger than the bore of the bushing on the side distal to the cap. Usually this will be an enlarged section of rod. However, one could stop on a nut threaded onto the section of rod near the side of the bushing distal to the cap and make a dispenser with an adjustable throw. In the case where the cap-to-barrel position is adjustable (rod threads into cap with a lock nut arrangement, for instance), then a nut on threaded rod arrangement on the proximal side of the bushing can be used to adjust the initial spring tension and the cap adjustment used to determine the throw. The limitations on this adjustment will be the fully compressed spring length and the uncompressed spring length.

Much of the feel is determined by the spring parameters. The spring rate (may be a constant rate, stepped rate spring, or other non-linear rate spring), initial compression, and throw of the dispenser (maximum travel when the cap is fully depressed) will primarily determine the feel of the dispenser. The longer the spring relative the throw of the dispenser the more even will be the pressure required to depress the cap, for a standard Hook's law spring. The up side of even pressure is that it is easier to fully unload the dispenser. The down side is that there is not as much tactile feedback about the position of the plunger, which becomes important when one dispenser load is used to fill more than one vaporizer.

Although not explicitly drawn into FIG. 15 for the sake of clarity, the portion of the barrel near the tip may be stuffed with a felt or similar material that can hold a lubricant, e.g., glycerin, so that each time the device is used a small amount of lubrication is carried toward the plunger and helps keep the rod and plunger from sticking. A porous bushing would also work well in this context.

The fact that this dispenser design has a lot in common with an ordinary ball pen opens up the possibility of dramatically reducing the manufacturing cost by modifying a high volume commercial product, like a ball pen, to be used as the tool body, so that only the tip and some internals are special.

The plunger design and tip design may be tailored to certain viscosity ranges and other rheological properties of the materials to be transferred. Nothing prevents the tip from being interchangeable so long as the rod can be removed from the cap easily. For example, the rod can have a slot in the end that threads into the rod so that a screw driver may be used to hold the rod from moving while the cap is twisted off Note that this embodiment has some limitations. For example, the rheology of the material must be such that the tip can be packed by pecking the material off of some surface. For example, bee pollen can be conveniently pecked from a cutting board, but the consistency of royal jelly would make it less convenient. Also, the tip has to be cleaned regularly or material will collect along the wall and it will eventually become hard to use. Further, while the design will keep the tip off the table, when not in use the tip should be covered. This limitation may be easily remedied by providing a cap that threads onto the tip or pushes onto the tip and is retained by some deformation based retention mechanism. Moreover, it cannot be used to dispense onto a hot surface without significant redeposition on the upper portions of the tip. It is also not easy to gauge how much material is being dispensed, meaning there is no adjustable stop mechanism or indicator of the position of the plunger beyond visually estimating how for the plunger has been pushed. This is another easily fixed limitation in that the barrel could be marked with graduations such as to give an accurate indication of how far the cap has been depressed. Furthermore, as drawn, the amount dispensed is a fixed quantity. The remedy for this limitation is to place a settable stop on the rod that replaces the current fixed retraction stop. Note that the ejection stop should be fixed because the plunger should extend the same distance beyond the mouth of the tip no matter what quantity of material is ejected. What determines the load volume is how far the plunger retracts into the mouth of the tip, assuming the user fills the entire available volume each time.

Figure 16:
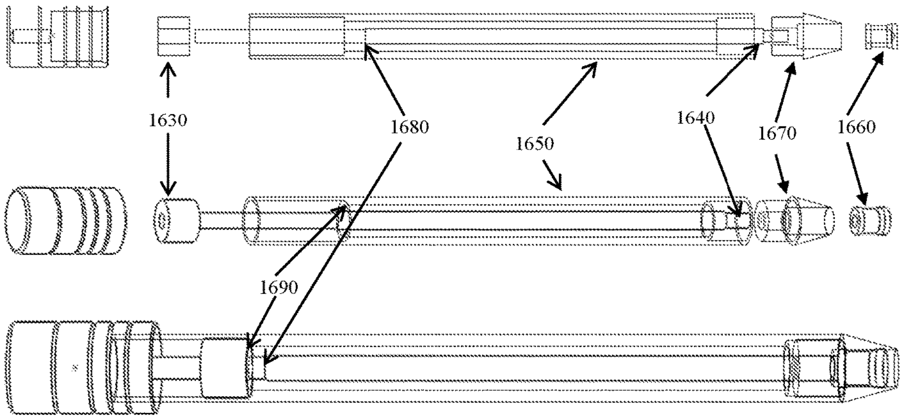
FIG. 16 includes wireframe views of a fully functional tool modeled after the design in FIG. 15.

FIG. 16 shows an embodiment of the loader tool that shows a number of useful features that allow it to be assembled and work reliably. Bushing 1630 presses into the barrel 1650 and stops on lip 1690. The plunger 1660 presses, glues, or threads onto the rod 1640. The reduction in bore diameter of the tip 1670 determines the maximum retraction of the plunger into the tip. However, if rod feature 1680 closes out on the bushing before the plunger hits the tip bore reduction, then feature 1680 determines the maximum plunger retraction. If instead of being a fixed position on the shaft, that stop is formed by another bushing with a set screw for instance, then the retraction extent of the plunger may be adjustable.

Figure 17A:
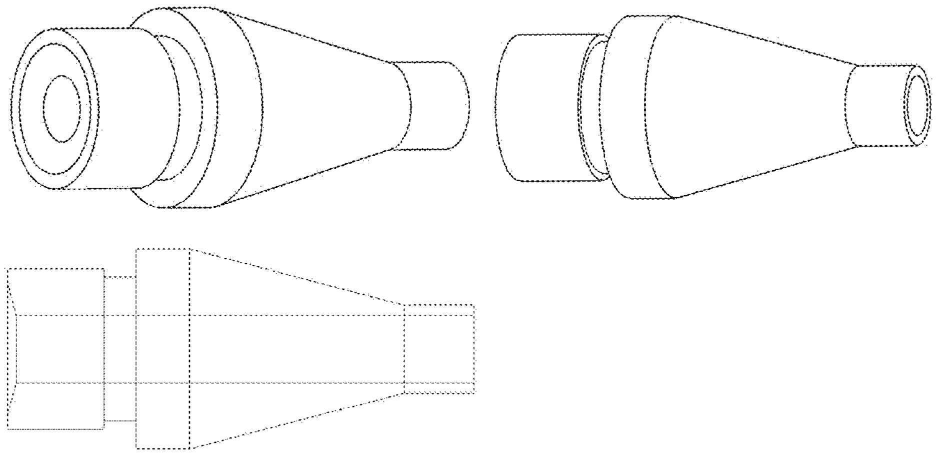
FIG. 17*a* shows three enlarged diagrams of a loader tip according to certain embodiments.
Figure 17B:
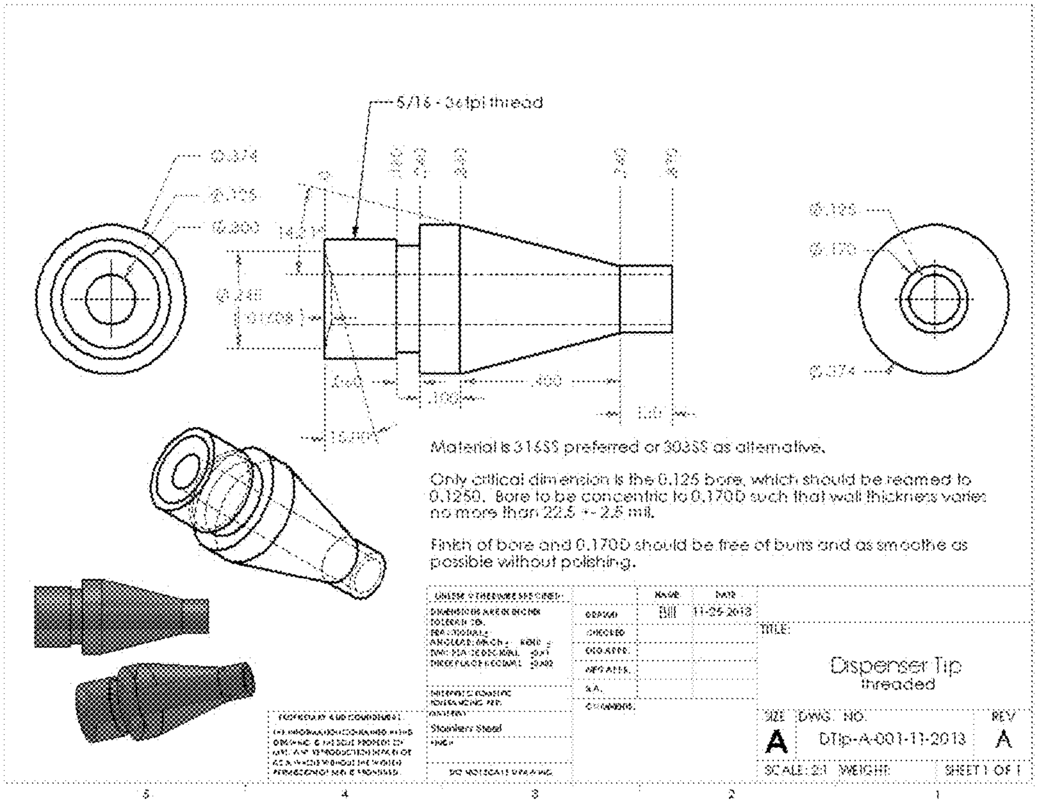
FIG. 17*b* is a mechanical drawing of the loader tip from FIG. 17.

A tip design closer to what is commercially viable is shown in FIGS. 17*a* and 17*b*, where FIG. 17*b* is a mechanical drawing so one may get a sense of scale. The tool in FIG. 16 is about 5" long and about 0.37" in diameter.

Following are a few alternative plunger design examples according to certain plunger design criteria.

There are no implied restrictions on the shape of the plunger end. The plunger as illustrated here has a flat end, but concave, convex, conical, spherical, parabolic, etc. are all potentially useful end profiles for certain applications.

Figure 18:
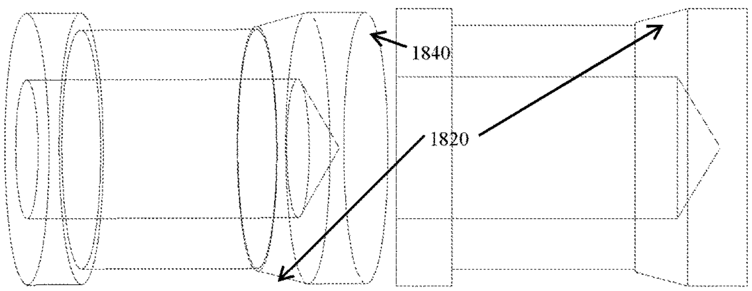
FIG. 18 is a wireframe drawing of a plunger with a flat face according to certain embodiments.

FIG. 18 shows one possible plunger structure in a semi-transparent manner so that the interior hole is visible.

The shape of the plunger is designed to maximize the stability of the slider. In this example there are two surfaces that ride on the wall of the bore. This maximizes the stability, while minimizing the surface area that touches the wall of the bore, thus reducing the friction between the plunger and the wall of the bore.

The tapered edge 1820 on the back side of the front guide 1840 of the plunger does not add much to the functionality at low temperatures, which is the case for the standard loading operation. However, when loading onto a hot surface and for versions of the tool specifically designed for loading while vaporizing (see later embodiments), the taper allows for drawing material that has accumulated on the wall of the tip bore to be melted and drawn off onto the plunger. This helps keep the mechanism working smoothly and increases the time between cleanings.

While design and base material choice go a long way toward achieving the desired properties from a use point of view, surface modification should not be overlooked. Although the material of choice, so far, is stainless steel, with 303SS/304SS [easy to machine] or 316SS [medical grade stainless steel], there are other choices of material and modifications of that material, either bulk or surface, that could work as well or better. A few of the more useful techniques are mentioned next, but is in no way intended to be exhaustive:

The surface tension (tackiness and adhesion of the material to be dispensed to the various surfaces of the tool) can be modified by surface treatments. Different portions of the tool may get different surface treatments based upon the intended use. For example, metallic surfaces may be nitrided, anodized, metallided, or plated (electroless plating, electroplating, or ion plating) depending upon the type of metal and desired effect. Non-metallic surfaces may receive different surface treatments, such as, plasma arc and/or covalently bonded coatings (parylene, acrylate, silane, silicone, etc.)

Efficacious surface treatments may be extended to the inside of the barrel and the plunger. Of course, there is nothing to prevent having different surface treatments on different portions of a given part, or from combining more than one surface treatment on a given surface. For example, one might titanium coat a steel tool and then nitride the coated tool to get a very durable surface that is somewhat self healing because of the high compressive surface stress created by the nitriding process. The look and/or function of the coating can be altered by incorporating binary and ternary nitride alloys. For example, titanium carbon nitride (TiCN), titanium aluminum nitride (TiAlN or AlTiN), and titanium aluminum carbon nitride may be used individually or in alternating layers with TiN. These coatings offer similar or superior enhancements in corrosion resistance and hardness, and additional colors ranging from light gray to nearly black, to a dark iridescent bluish-purple depending on the exact process of application. Boron and zirconium nitrides have other potentially useful properties depending upon the application.

Nitriding and carbonitriding, (via gas, plasma, or salt bath) hold special interest for steels and stainless steels and titanium because of the highly compressive self-healing nature of the resulting surface. Nitriding of aluminum surfaces allows for maintaining excellent thermal conductivity, yet having an environmentally resistant surface, for those applications where high thermal conductivity is important. Similar surface properties can be obtained by boriding.

When using any of the tools to dispense directly onto heated surfaces, the surface treatment(s) and bulk material (s) that the rod, tip, and umbrella nut are made from will significantly affect the performance of the tool. The design of the tip will also affect the thermal performance. The two most important features in regard to the static tool's tip design are the wall thickness of the portion forward of the umbrella nut and the length and thickness of the portion immediately behind the umbrella nut, where forward refers to direction of the tip end where the material to be vaporized is dispensed. The length and thickness of the portion immediately behind the umbrella nut and type of material the tip is made from will determine how fast the heat is transferred away from the active region or region of interest, which is the portion forward of the umbrella. In the case of dynamic loaders, the material properties, particularly thermal conductivity, of the rod to which the plunger is attached, material properties of the plunger and material properties of the wall of the bore that the plunger rides in will determine how the transfer material behaves while loading onto a hot vaporizer. (Please note that these examples and are in no way intended to limit the scope this application.)

The above discussion would not be complete without a detailed consideration of the consequences of the non-Newtonian fluid behavior of the transfer material. Viscosity has been used rather loosely in the previous discussion, so a brief digression is in order to clarify the rheological boundaries of the materials that one might dispense. The following graphs and illustrations will help with the ensuing discourse. First, a couple definitions:

Newtonian fluids—have a viscosity that is independent of the shear rate and can be considered a material constant. This is equivalent to the relationship between shear stress (force trying to move the fluid) and shear rate (resulting change in fluid velocity due the force that is trying to move the fluid) being linear. This is approximately true for most solvents and dilute dispersions or solutions.

Non-Newtonian fluids—have a viscosity that varies with shear rate, which implies that measurement at one shear rate is not sufficient to completely characterize the viscosity. Generally the viscosity is presented as a flow diagram where shear stress is plotted against shear rate or viscosity is plotted against shear rate.

Figure 32:
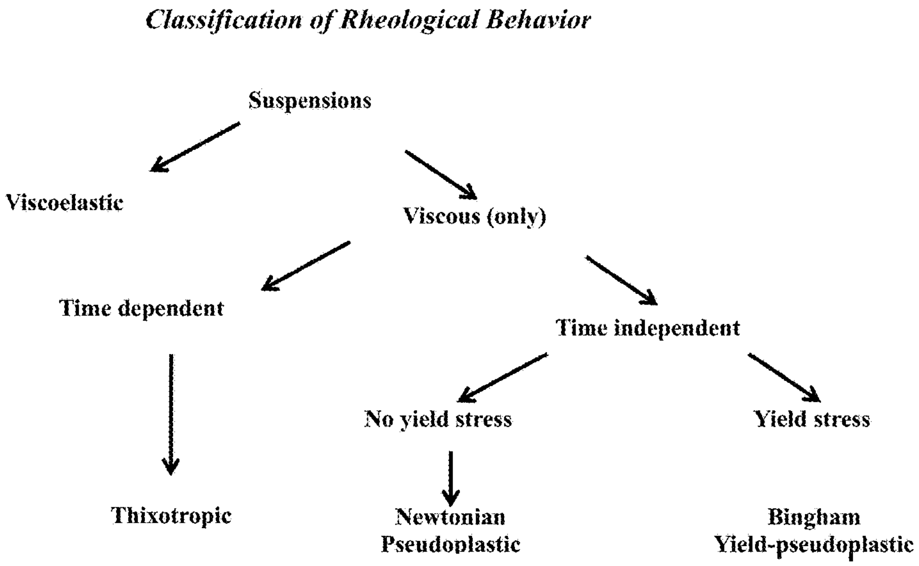
FIG. 32 is a rheological classification scheme according to certain embodiments.

The classification scheme in FIG. 32 should help clarify the relationships between the various categories of rheological behavior.

The following table shows what the above classification system means in more practical terms by relating the behavioral terminology to familiar substances.

| | Shear Thinning | Shear Thickening |
|---|---|---|
| time-dependent (memory materials) | thixotropic ketchup, honey | rheopectic printer's ink |
| time-independent (memoryless materials) | pseudoplastic styling gel, paint | dilatant cornstarch paste, silly putty, quicksand |
| yield stress | Bingham plastic toothpaste, molten chocolate, blood | |

Figure 33:
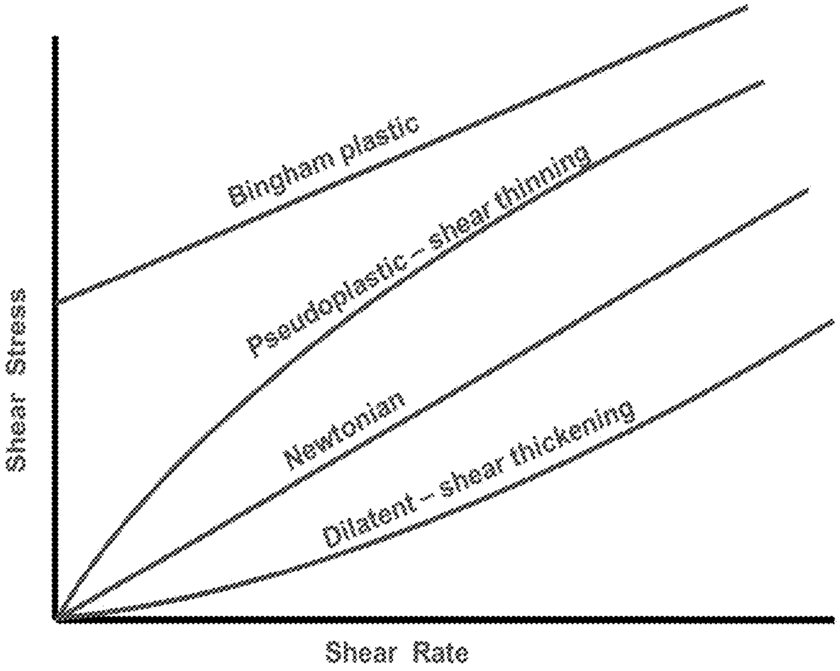
FIG. 33 is a plot illustrating the relationship between shear stress and shear rate for various common rheological classifications.
Figure 34:
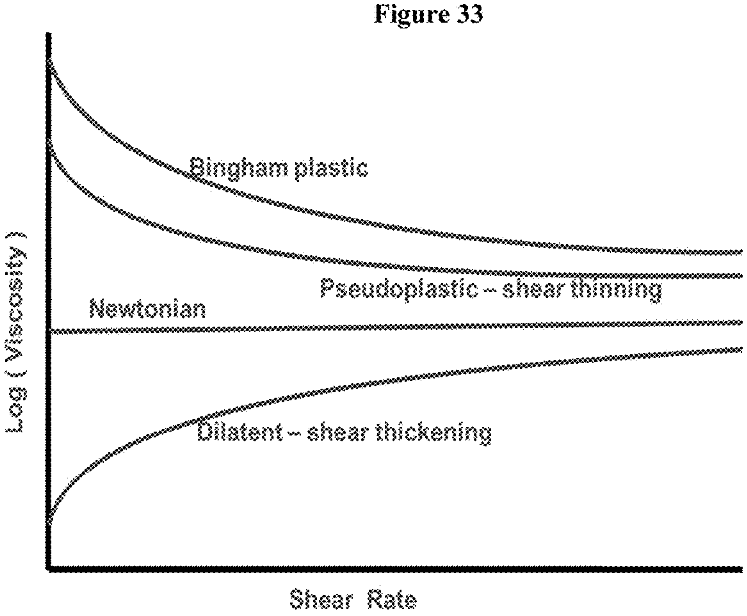
FIG. 34 is a plot illustrating the relationship between viscosity and shear rate for various common rheological classifications.

Almost all of the materials being transferred will have significant non-Newtonian behavior. Most common behaviors will fall into the shear thinning category. This relates to molecular networks being broken down by mechanical motion of the fluid. As the intertwined networks break down the fluid thins and becomes more pliable. One of the consequences for tip design is that the simple cylindrical well will work fine, and as noted earlier this results in a more complete ejection of the material. FIGS. 33 and 34 may help to understand the relationship between shear stress and shear rate and the common rheological classifications in the above table and FIG. 32.

In the case of shear thickening, dilatant behavior, mechanical agitation causes particles to flocculate or otherwise stick together, resulting in a thicker less pliable fluid. One consequence of this behavior on the design of the tip is that the three hole well will work better because the ejection rod is shearing less fluid. The fact that the ejection rod is also guided in its travel will make inhomogeneity in the fluid irrelevant. Shaping the end of the ejection rod so that it has a cutting behavior that minimizes the lateral shearing effects will make ejection easier and smoother.

Figure 19:
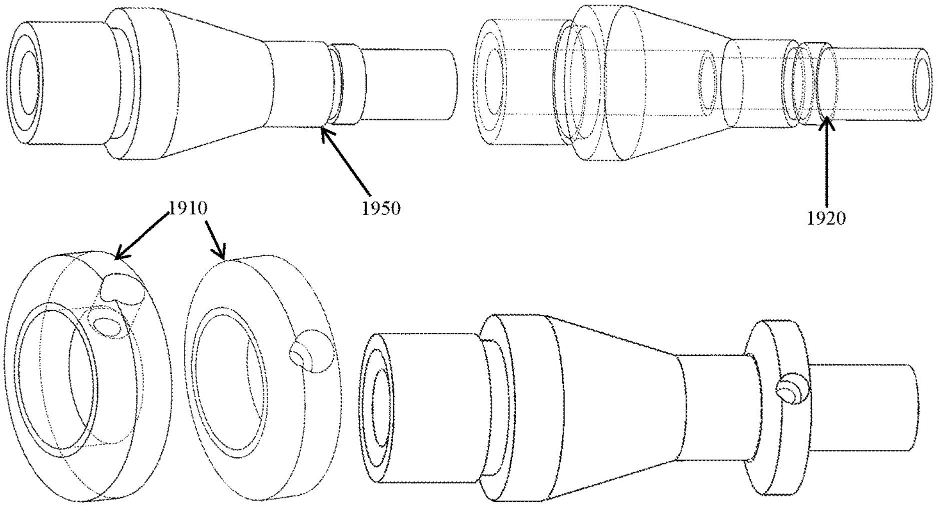
FIG. 19 is a wireframe view of the DR tip in both the assembled and apart states according to certain embodiments.

Recall that item 4 in a previous note about some limitations of the simple push plunger design, it was noted that using the tool to dispense onto a hot surface would likely result in significant redeposition of the transfer material onto the outside of the tip. One possible embodiment that ameliorates this problem by building upon the umbrella concept developed for the static tools follows. The following design variation shows that one can make a dynamic dispensing tool that has dual use in that it can be configured to load cleanly and efficiently on a cool surface or a hot surface. Thus, the tool can be configured to apply material to an actively vaporizing surface or non-destructively, meaning without damaging the heating element, load a hand held vaporizer. FIG. 19 illustrates the general idea, where threads 1920 have been added to the nose of the tip so that the umbrella 1910 may be threaded on as needed. The umbrella has a small hole for a pin wrench to assist in tightening or loosening. The umbrella closes out on surface 1950. The umbrella may be knurled to facilitate removal with only one's fingers. The tradeoff is that knurling will make cleaning the tool head a little harder.

Figure 20:
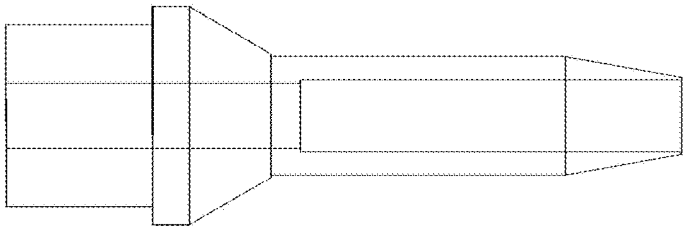
FIG. 20 are diagrams of a long nose version of the loader tip designed for loading hand held vaporizers according to certain embodiments.

In the case of hand held vaporizers the loading well may be fairly deep and usually not very large in diameter. The slender elongated tip of FIG. 20 is specifically designed to address this application. Although not shown in the figure, a threaded section could be added to attach an umbrella nut when the tool is not being used to load hand held vaporizers.

Figure 21:
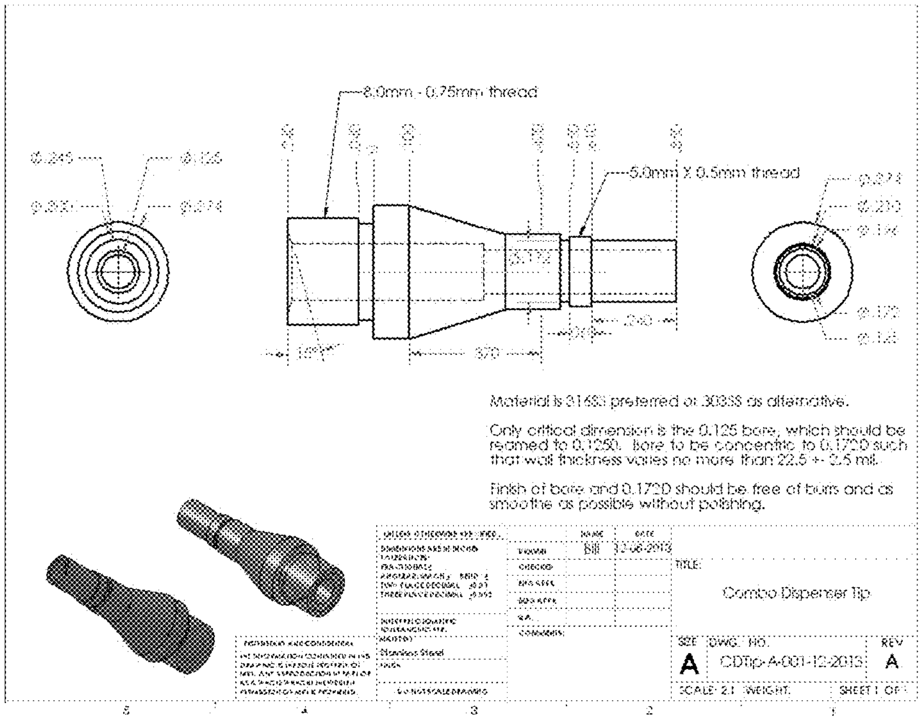
FIG. 21 is a mechanical drawing of the DR tip with a threaded nose for optional attachment of the umbrella according to certain embodiments.
Figure 22:
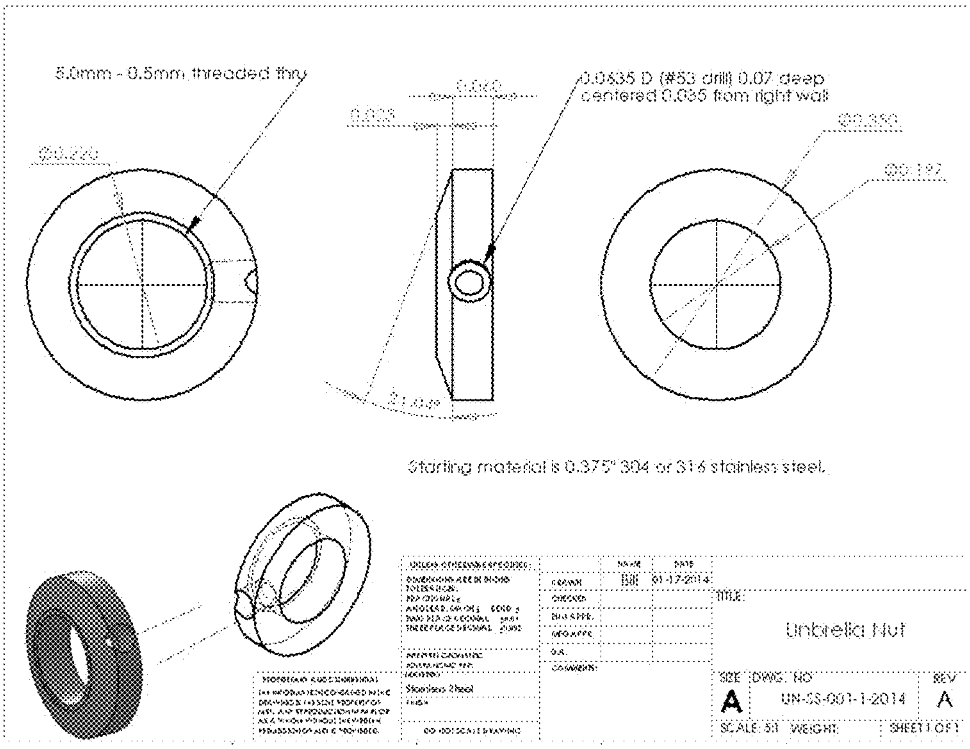
FIG. 22 is a mechanical drawing of the detachable umbrella according to certain embodiments.

FIGS. 21 and 22 give the detailed drawings with dimensions of the DR tip and umbrella nut.

The examples above use a manual push mechanism, much like a standard syringe, except that this one is spring loaded for automatic return. However, it is possible and in many cases desirable to use a twist mechanism instead of the manual linear depression mechanism. The twist mechanism has an advantage in that it can have a great mechanical advantage (multiplying the manually applied force many times. Thus, allows more use without fatigue. This mechanical advantage significantly extends the viscosity range of materials that can be used with the dispenser. This is particularly true when the dispenser consists of a reservoir that is significantly larger than the dispenser tip. Note that there is nothing implied here preventing the twist and linear push mechanisms from being combined.

An example of one such possible combination of linear push with twist is having the cap of a device that externally looks the same as in FIG. 16, drive a very coarse pitch thread that in turn drives a much finer pitch thread, where the fine pitch thread drives the plunger that dispenses the material into or onto the vaporizer. For clarity, as the cap moves linearly up and down, a twisted shaft is forced to rotate. The end of the twisted shaft that is distal to the cap, inserts as a spline into a finer pitch slug that drives the plunger. The twisted shaft may even spline directly into the plunger depending on exactly how the mechanism is designed.

Figure 23:
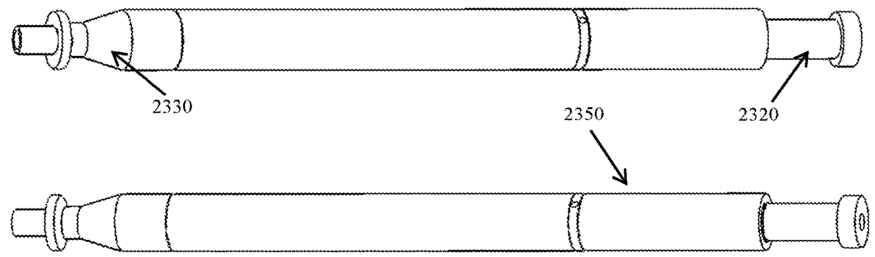
FIG. 23 is a line drawing of the TC loader tool that can be used to fill the tip from an internal reservoir by twisting the twist driver and dispenses by depressing the thumb depressor according to certain embodiments.

FIG. 23 shows a loader tool that dispenses the load by pushing the thumb depressor 2320, while the quantity to be dispensed is determined by twisting feature 2350. The concept of loading and then dispensing implies that, unlike previous tool embodiments, this embodiment has an internal reservoir for the transfer material that can hold a sufficient quantity of material for multiple doses. The size of this embodiment is 5.6" long and 0.37" in diameter. There are many possible variations on this theme.

Further variations and combinations may include: 1) a retractable tip, 2) threads on the outside of the tip so that a cap can thread onto it, 3) threads on the umbrella nut so that a cap can thread onto it, 4) a scale on the twist section that shows how much is metered out vs. amount of rotation, and 5) a more automated method of moving the plunger, e.g., a solenoid, air cylinder operated by compressed gas, or a small motor.

It is worth noting that twisting is an example of a mechanism for multiplying the force a person may comfortably apply to the plunger. The threads provide an a significant mechanical advantage. Variation 5, listed above, contains further examples of means for multiplying the force applied to the plunger. There is nothing implied here that limits such force multiplication mechanisms to these few examples. For example, merely decreasing the area of the plunger, while using the same motive mechanism, is a method of increasing the force multiplication factor.

Since the umbrella nut thickness is insufficient to stably hold a threaded cap, variation 3 above works by designing the cap to close out on the tapered portion of the tip 2330. The combination of threads on the umbrella nut forcing the cap against the tapered portion of the tip will hold the cap in a stable fashion. Note that this solution enables the cap to be a smaller diameter than variation 2, where the outside of the tip is threaded, which implies that the cap must be greater diameter than the rest of the tool.

Note the tool could have been designed such that the amount metered out is determined by how far the thumb depressor can be depressed. Since the thumb depressor stops when the wide head hits the top of the twist driver, a simple way to vary the travel of the thumb depressor is to allow it to be threaded more or less onto the upper rod. This approach has the undesirable consequence of the rod not necessarily clearing the throat of the tip, meaning not extending slightly beyond the end of the tip when the thumb depressor is fully depressed, which implies that the throat of the tip always has material left in it that may leak out or become stale between uses. This is why in the embodiment here the throw of the rod is fixed and the amount of transfer material dispensed each time is determined by the rotation of the twist driver.

Figure 24:
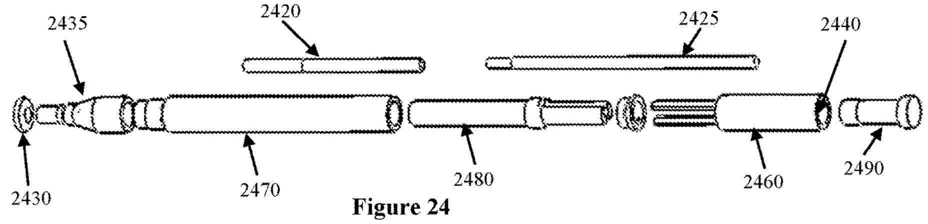
FIG. 24 is an explode view of the TC loader of FIG. 23.

For a more detailed look at the mechanism of this embodiment the exploded view of FIG. 24 will be used. The lower 2420 and upper rods 2425 are normally joined. The turned down section at the left end of the upper rod is either cemented or pressed into a corresponding hole in the lower rod so that they act as a single rod when assembled. Also, the right hand end of the upper rod that is fixed to the thumb depressor is threaded. Threading the rod assembly into the thumb depressor allows the tool to be disassembled for cleaning. Threading the join of the upper and lower rods can achieve the same ease of disassembly.

The tool is loaded by removing the tip 2435, retracting (by twisting) the plunger 2480 as far as it will go, and filling the barrel 2470 through the end that the tip threads onto.

How it Works:

Referring to FIG. 24, the material to be dispensed is stored to the left of the plunger 2480 and will surround the section of the rod (assembly of 2420 and 2425) that passes through this section. When the twist driver 2460 is turned, the plunger will advance toward the tip forcing material in that direction, through the loading bay 2510, and ultimately into the dispensing throat 2520 (also called just the throat). This assumes that the material is relatively incompressible and that the rod is retracted so that there is somewhere for the material to go. Note that the rod retracts further than the entrance to the dispensing throat 2530, so that the rod will never become misaligned to the dispensing throat. Once throat has been loaded with the desired amount of material, the thumb depressor 2490 is depressed until it stops on the entrance to the spring well 2440. When the thumb depressor is fully depressed the left end of the rod will protrude slightly beyond the end of the tip, allowing all the material that was in the throat to be ejected. Note that depending upon the compressibility of the material, when the rod first starts to advance, some material may be forced back into the loading bay. So the ejected volume will have some dependence on the compressibility of the material being dispensed.

Figure 25:
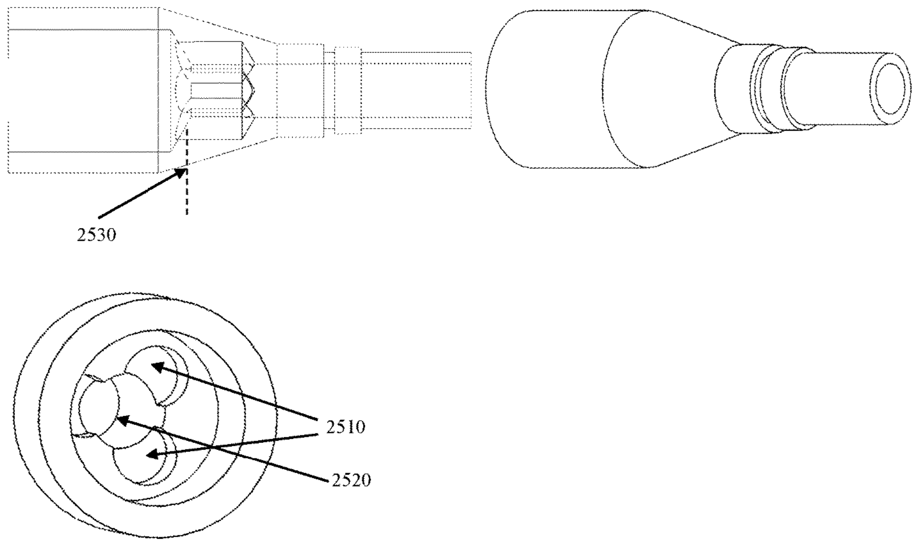
FIG. 25 includes a set of line drawings showing details of the TC loader tip.

There are many possible variations on the loading bay. For example, it could be a simple cylindrical depression concentric with the dispensing throat. The advantage of this simpler configuration is that for applications where the material being dispensed is changed frequently, it is easier to make the plunger end fit the loading bay so that virtually all the material is ultimately dispensed resulting in very little waste. An advantage of the FIG. 25 design is that the three remaining portions of ejection bore (refers to that section of the throat that overlaps with the loading bay) guide and steady the plunger, and help shear the more viscous materials during ejection. Clearly, there may be reasons to offer more than one version of this tool given the wide range of applications and wide range of materials that one may want to dispense. From the figure it can be seen that the holes are drilled, not milled, because this makes the hole more funnel like and can handle viscous material better.

Figure 26:
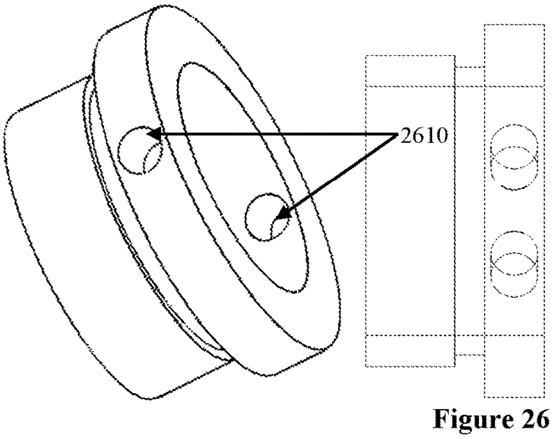
FIG. 26 is diagram illustrating a couple of views of the TC loader retaining ring according to certain embodiments.
Figure 27:
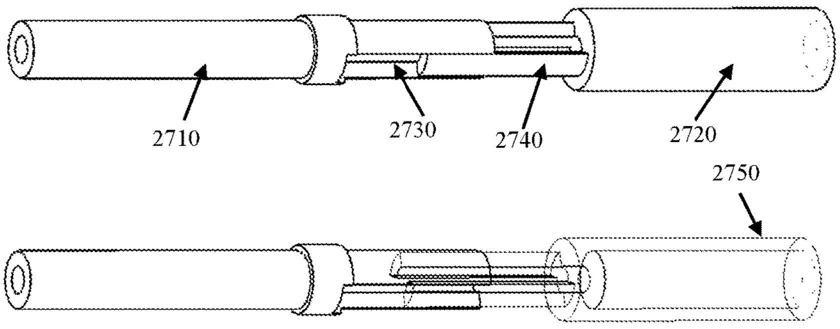
FIG. 27 includes a couple of line drawings indicating the salient features of the TC loader's spline gear drive mechanism according to certain embodiments.

The retaining ring of FIG. 26 holds the plunger 2710 in the barrel and essentially keeps the tool from coming apart when forcing material into the throat of the tip. The two holes 2610 (3/64" diameter) are for tightening or loosening the retainer. 3/64" allows for use of standard drill rod or 1 mm (up to 1.1 mm) rod, where metric is popular. As the twist driver 2720 turns the plunger the plunger, which threads into the barrel, needs to advance axially while the twist driver remains axially stationary. One mechanism that allows this to happen is the spline gear 2730 & 2740 that in this case consists of two intertwined forks. The rod resides in the center of this assembly and is not shown is the illustration for the sake of clarity. The spring that fits into the spring cavity 2750 must also fit over the rod without interference. The spring keeps tension on the twist driver, while the lower rod stopping on the plunger keeps the tool from coming apart.

Following are description of a few exemplary design features according to certain embodiments.

The tip, lower rod, barrel, and plunger should be made out of a material that is not toxic, since these surfaces touch the material that is being dispensed. Common candidate materials are stainless steel, titanium, ceramic, certain plastics, e.g, PTFE. The other pieces may be made out of any material that is sufficiently durable.

The threaded and therefore detachable umbrella nut allows the tool to serve the dual purpose of loading material onto a relatively cool surface and also allows the tool to be used for loading material onto a hot surface where the material is vaporizing during the loading process.

The twist mechanism and plunger can apply very significant pressure to the material being dispensed. By changing the thread pitch of the barrel and plunger one can determine how much force can be applied to the material being loaded. Materials that are paste like may require such force as to require very fine pitch threads.

FIG. 26 shows a retaining insert with two holes for tightening or loosening. This allows the tool to be disassembled for maintenance or cleaning.

Figure 28:
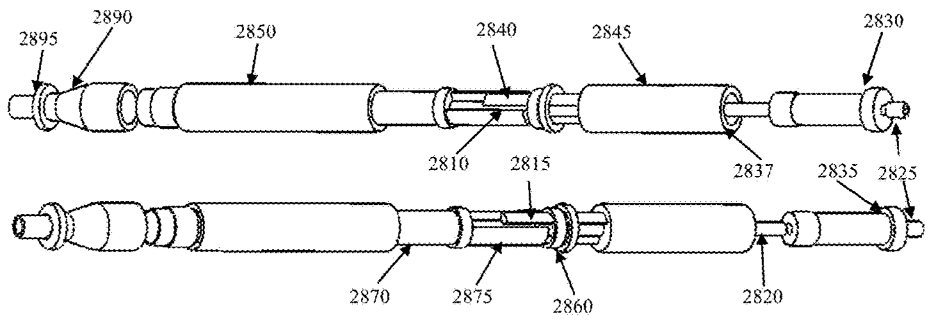
FIG. 28 shows a more advanced version of the TC loader that among other improvements allows the user to adjust the throw and thus the amount dispensed without having to partially depress the cap (e.g., a thumb depressor) according to certain embodiments.

A potential criticism of the embodiment described above is that the rod stops on a movable part, the plunger. A design could be made that does not suffer this weakness and is illustrated in FIG. 28:

The rod could be a single piece and has a short slot for a small fin insert that causes the rod to stop against the retaining nut that does not move with the plunger. The small fin could also be replaced by a small diameter pin that fit into holes in the rod that are drilled perpendicular to the axis of the rod. The diameter of the rod can then be uniform along its entire length. (Makes manufacturing significantly easier.)

If instead, the rod is constrained to rotate with the plunger, there is a reduced risk of material being trapped between the rod and plunger. A nuance that would lengthen the time between cleanings is surface treating the rod in such a way as to lower the tack to the material being dispensed. It is worth noting that most of the materials being dispensed will be non-Newtonian fluids and as such their rheological properties beyond simple surface tension become important, if not dominant, design considerations.

In the previous design the rod threads into the cap because if it were press fit the tool would be hard to disassemble and clean. In this version, the rod could be pressed into the cap, or otherwise fixed permanently to the cap, and the tool would still be easy to clean.

Alternatively, threading the rod into the cap allows for a design where the user is able to adjust the throw of the rod. One possible embodiment would be to drill and thread the cap all the way through and include a short set screw for locking the rod in place after the desired throw length was set by simply twisting the cap while holding the twist driver in place. Once the throw is set, the rod is then locked in place by tightening the set screw. Note the set screw is in line and not perpendicular to the rod. So the set screw uses the same threaded hole in the cap as the rod. Such an arrangement of rod and set screw, make the total useful adjustment approximately the length of the cap minus twice the length of the set screw. (Here it is assumed that the minimum length of rod threaded into the cap should be about the length of set screw.)

The retaining ring 2860 threads into the barrel 2850 and the diameter of the bore of the retaining ring is such that the forks 2840 of the twist driver 2845 can pass through the bore (0.250 OD), but the forks 2875 of the plunger 2870 (0.259 OD) cannot and neither can the pin 2810 in the rod 2820, since the pin is also 0.259" long. So the pin in the rod stops on the retaining ring, which in turn stops the spring (not shown in the drawing—but resides in the same twist driver cavity that the cap rides in when the tool is together) from pulling the rod out of the barrel. How far the cap is threaded onto the rod determines the throw by setting the distance the cap can move before the wide portion of the top stops on the end of the twist driver. Notice that the rod pin is captured between the tines of the forks forcing the rod to rotate with the plunger, which minimizes the chance for material to creep between the rod surface and plunger surfaces causing them to stick and make the plunger action more difficult. The ejection end of the rod, the portion that travels in the tip throat, can be relieved in such a way as to minimize contact with the plunger wall, making the reasoning here very similar to the reasoning behind the design of the plunger tip depicted in FIG. 18. Finally notice that with this adjustment method the rod always retracts to the same position. The adjustment merely determines where the rod stops when the cap 2830 is fully depressed. The other way to design this is to make the rod in the depressed state always stop in the same position, which has the advantage of never leaving material in the throat of the tip after use.

Figure 29:
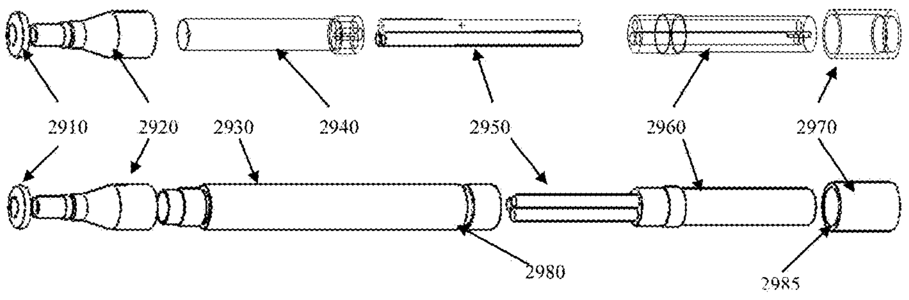
FIG. 29 includes line diagrams of a twist only tool that dispenses by twisting the twist driver section of the tool, which, according to certain embodiments, is a simpler tool and accomplishes essentially the same task as the TC loader.

For many materials a simple twist dispenser version of the above may be all that is required. This would have all the features of the above example, except that there is no spring loaded cap for pushing the material out. The material is pushed out by twisting the twist driver directly instead of using the twist driver to push the material from the loading bay to the throat region. An example embodiment is shown in FIG. 29 below. The tool is composed of 6 types of components including the brim 2910 and the tip 2920, where the rods are repeated 3 times and the wavy spring washer that applies continuous force to the twist diver is not shown.

Important design features relating to form and function of the tool: The plunger 2940 is threaded into the barrel 2930. There are 3 0.1" diameter rods 2950 that are press fit and/or glued into the back of the plunger. The same three rods slip fit into the twist driver 2960. Note that when assembled the retainer cap 2970 slips over the twist driver. There is a small hole in the top of the twist driver to prevent any pressure or vacuum buildup. The retainer cap base 2980 closes out on the barrel surface 2985 and holds the twist driver against a wavy washer (not shown in the figure) that gives the twist driver proper feel in the sense of torque required to move the drive mechanism (plunger, rods, twist driver). Thus, as the twist driver is rotated the rods and plunger are also constrained to rotate with it, resulting in the plunger being driven forward or backward, depending upon the direction of twist.

Figure 30:
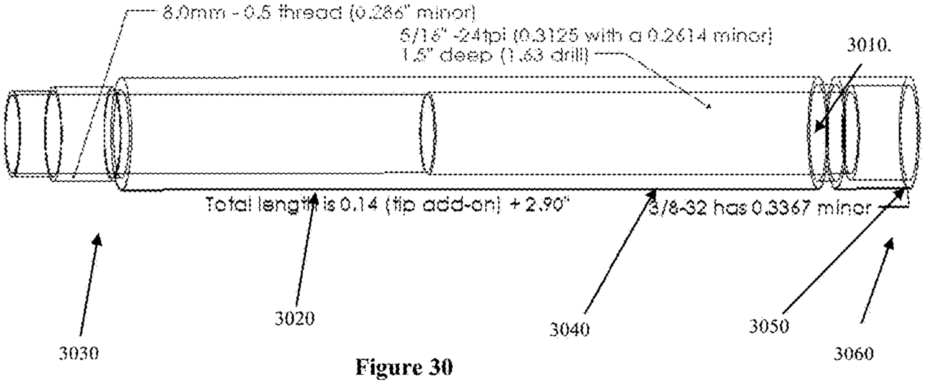
FIG. 30 shows some mechanical details of the barrel section of the twist only tool according to certain embodiments.

For the sake of clarity some critical features of the barrel design are shown in FIG. 30. The material to be dispensed is loaded into cavity 3020, which is a close fit, but still a slip fit, to the smooth part of the plunger. The retainer cap 2790 closes out on surface 3010. The threaded end of the plunger, which is also the end that the three rods press fit into, threads into section 3040 of the barrel. The tip threads onto the 8.0 mm by 0.5 mm threads 3030. The fork of the twist driver is a slip fit for bore 3050 and is held in place by the retaining cap that threads onto 3060. The material to be dispensed is loaded into section 3020 ahead of the plunger, which also will project into section 3020.

The tool loads by unscrewing the tip and using the twist driver to screw the plunger back until it stops or there is enough space to load the desired quantity of material. The tip is screwed back into place and the tool is ready for use. So as not to clutter the illustrations, a push on or screw on cap that covers the tip (including the umbrella nut) when not in use, an optional but generally desirable feature, is not shown in the illustration. The cap may have a method of plugging the end of the tip (silicone in the bottom of the cap for example) so that relatively low viscosity material cannot leak out when not in use. This is also useful for those occasions when the tool is left in a place where it is allowed to heat up to a point that significantly reduces the viscosity of the material stored inside. Although three rods are shown here as the pseudo-spline drive mechanism, two rods, one square rod, a common spline gear, can all do the same job. The point is that in this tool the plunger is driven by a spline like mechanism and the twist driver is held in place by a retainer cap.

Again for clarity of illustration, the knurled surfaces are not depicted as such in the illustrations. The retainer cap and the twist driver are both knurled on the outside surfaces that are intended to be gripped.

Another detail not addressed in the illustrations is some mechanism for keeping the retainer cap from unscrewing while the twist driver is being turned. There are many ways to do this besides the obvious star or lock washer. For example, the bottom of the retainer nut can be machined to lock against the closing surface. Another way is to taper both closing surfaces in a way that is locking and/or partially swaging so that the force required to undo the retainer cap is significantly greater than any force twisting the twist driver will create.

Figure 31:
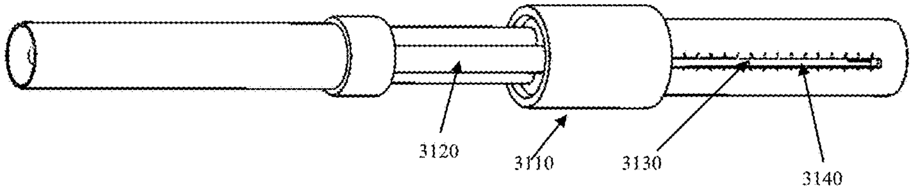
FIG. 31 shows an enhancement to the previous version of the twist only tool where there is an indicator that lets the user know how much material is being dispensed and how much is left in the tool reservoir.

Just as with the previous example, further variations and combinations may include 1) a retractable tip, 2) threads on the outside of the tip so that a cap can thread onto it, 3) threads on the umbrella nut so that a cap can thread onto it, 4) a scale on the twist section that shows how much is metered out vs. amount of rotation. The problem of measuring how much material has been metered out can be handled in any number of ways, but a particularly simple way is illustrated next in FIG. 31.

One of the rods 3120 is used as an indicator of the position of the plunger in the barrel 3110 and thus the quantity of material left in the barrel. The marks along the slot 3140 are graduations for measuring the position of the end of the rod 3130 and thus the plunger position in barrel.

It should be noted that although the tip, retainer cap, and retaining ring use threads in the examples to attach to the rest of the tool, the threads could be replaced by other attachment schemes. For example, a twist lock against a wavy washer would also work well and may be more forgiving in the sense that it would not stick as easily as threads if some of the material to be dispensed happened to get onto one of the surfaces.

It should be noted that retraction as a means of isolating the active and possibly messy end from the surroundings (like a purse, clothing, or table top) may be extended to all manner of tips, whether hollow for active dispensing or not.

Not previously mentioned, but may improve the flexibility of use of the tool, is the fact that the range of materials that may be effectively metered out is significantly increased by the fact that the tip and rod end that engages the tip may be changed out without affecting the other parts of the tool. Thus, there is the possibility of using large diameter bore tips for dispensing highly viscous material and switching to small bore tips for less viscous material.

The examples above are in no way intended to limit the scope of this application. For example, instead of loading the tool manually through the end, a tool could be designed to use cartridges preloaded with the material to be dispensed.

The cartridge has certain advantages (including but not limited to): 1) Cartridges enable changing the material being dispensed without much mess or waste; 2) Cartridges make it easy to know how much material is being loaded into the tool; 3) Cartridges make it easy to keep track of what material is in the tool since cartridges can be color coded, bar coded, or otherwise marked to identify the contents; 4) Cartridges provide a uniform, clean, easy way for merchants to sell the material to be dispensed; and 5) Cartridges can be disposable, which would allow both a convenient and hygienic way distributing the material.

Although the examples above are of standalone tools, there is no implied limitation to such venue. For example, the twist only version could easily be adapted to fit onto a hand held or table top vaporizer in such a way as to meter out material directly onto the vaporizing element. In the case of table top vaporizers or hand held vaporizers where the vapor is extracted from the side, the twist click dispenser could also easily be adapted.

Surface treatments and thermal properties: So far only brief mention was made of using the tool to dispense directly onto heated surfaces. The surface treatment(s) and bulk material(s) that the rod, tip, and umbrella nut are made from will significantly affect the performance of the tool and this is particularly true when using the tool to deposit the material to be dispensed directly onto a heated surface. A few salient points follow: (please note that these examples and are in no way intended to limit the scope of this section of the application)

The design of the tip will also affect the thermal performance. The two most important features in this regard are the wall thickness of the portion forward of the umbrella nut and the length and thickness of the portion immediately behind the umbrella nut, where forward refers to direction of the tip end where the material to be vaporized is dispensed. The length and thickness of the portion immediately behind the umbrella nut and type of material the tip is made from will determine how fast the heat is transferred away from the active region or region of interest, the portion forward of the umbrella.

The surface tension (tackiness and adhesion of the material to be dispensed to the various surfaces of the tool) can be modified by surface treatments. Different portions of the tool may get different surface treatments based upon the intended use. For example, metallic surfaces may be nitrided, anodized, metallided, thermal sprayed, or plated (electroless plating, electroplating, or ion plating) depending upon the type of metal and desired effect. Non-metallic surfaces may receive different surface treatments, such as, plasma arc and/or covalently bonded coatings (parylene, acrylate, silane, silicone, etc)

Efficacious surface treatment may be extended to the inside of the barrel and the plunger. Of course, there is nothing to prevent having different surface treatments on different portions of a given part, or from combining more than one surface treatment on a given surface.

Nitriding and carbonitriding hold special interest for steels and stainless steels and titanium because of the highly compressive self healing nature of the resulting surface. Nitriding of aluminum surfaces allows for maintaining excellent thermal conductivity, yet having an environmentally resistant surface, for those applications where high thermal conductivity is important.

What is claimed:

1. An apparatus designed for manual transfer of a viscous fluid, comprising:

a tip having a depression to accommodate an amount of the viscous fluid;

a brim to cause a break in a vapor trail when the amount of viscous fluid is being placed on a heated surface and becomes vaporized;

a handle to allow a user to hold the tool without contacting the tip;

wherein the depression has a conical shape and a circular lip that is coaxial with the brim; and wherein the tip comprises a threaded tail for attaching to the handle, a shank with a reduced diameter relative to the tail, and a tapered portion between the threaded tail and the shank.

2. The apparatus of claim 1, further comprising a cap that fits over the tip to prevent unwanted transfer of any remaining viscous fluid to surroundings when the tool is resting on a surface, wherein the cap is a screw on cap.

3. The apparatus of claim 1, wherein the handle is hollow to accommodate one or more useful tools.

4. The apparatus of claim 1, wherein the handle is hollow to accommodate an additional amount of the viscous fluid.

5. The apparatus of claim 1, wherein the tip, and the handle are made of different materials.

6. The apparatus of claim 1, wherein the handle includes a threaded end to allow the user to easily replace the tip.

7. The apparatus of claim 1, further comprising a pagoda structure for dissipating heat from the tip.

8. The apparatus of claim 1, wherein the brim comprises an umbrella washer or nut acting as a lock nut to hold the tip at a user selected point on the end of the handle, thereby allowing adjustable thermal management of the tip.

9. An apparatus designed for manual transfer of a viscous fluid onto a hot surface, comprising:

a tip having two oppositely-facing ends, an exterior surface between the two oppositely-facing ends and a depression formed in one of the two oppositely-facing ends, wherein the depression is configured to accommodate an amount of the viscous fluid and to release at least a portion of the amount of the viscous fluid when the tip is brought to the hot surface;

a brim near the other of the two oppositely-facing ends of the tip and configured to cause a break in a vapor trail along the exterior surface of the tip when the amount of viscous fluid becomes vaporized; and a handle to allow a user to hold the apparatus without contacting the tip; and a shank connecting the tip to the handle, wherein the shank has a tapered portion and a straight portion with a reduced diameter, and wherein the other of the two opposing ends of the tip is hollow and fits over a portion of the shank.

10. The apparatus of claim 9, wherein the portion of the shank that fits inside the tip is adjustable.

11. The apparatus of claim 9, further comprising a cap that fits over the tip, the brim and the shank.

12. The apparatus of claim 9, wherein the brim comprises an umbrella nut that locks the tip in place.

13. The apparatus of claim 9, wherein the shank has a pagoda structure thereon for dissipating heat from the tip.

14. The apparatus of claim 9, wherein the exterior surface between the two oppositely-facing ends has a cylindrical shape.

15. The apparatus of claim 9, wherein the depression has a conical shape with a flat or round surface near an apex of the conical shape.

16. The apparatus of claim 9, wherein the exterior surface of the tip is fluted.

17. An apparatus designed for manual transfer of a viscous fluid onto a hot surface, comprising:

a tip having two oppositely-facing ends, an exterior surface between the two oppositely-facing ends and a depression formed in one of the two oppositely-facing ends, wherein the depression is configured to accommodate an amount of the viscous fluid and to release at least a portion of the amount of the viscous fluid when the tip is brought to the hot surface;

a brim near the other of the two oppositely-facing ends of the tip and configured to cause a break in a vapor trail along the exterior surface of the tip when the amount of viscous fluid becomes vaporized;

a handle to allow a user to hold the apparatus without contacting the tip; and wherein the tip has a hole between the exterior surface of the tip and an inner surface in the depression.

18. The apparatus of claim 17, further comprising a shank connecting the tip to the handle, wherein the shank has a tapered portion and a straight portion with a reduced diameter.

19. The apparatus of claim 18, wherein the other of the two opposing ends of the tip is hollow and fits over a portion of the shank.

20. The apparatus of claim 19, wherein the portion of the shank that fits inside the tip is adjustable.

* * * * *